United States Patent
Ye et al.

(10) Patent No.: US 11,738,062 B2
(45) Date of Patent: Aug. 29, 2023

(54) HERBAL MEDICINE EXTRACTS AND USES AND METHODS OF PREPARATION THEREOF

(71) Applicant: ALPHA OASIS LLC, Louisville, KY (US)

(72) Inventors: Hong Ye, Louisville, KY (US); Chengbao Ye, Hubei (CN)

(73) Assignee: ALPHA OASIS LLC, Louisville, KY (US)

( * ) Notice: Subject to any disclaimer, the term of this patent is extended or adjusted under 35 U.S.C. 154(b) by 149 days.

(21) Appl. No.: 17/271,567

(22) PCT Filed: Aug. 26, 2019

(86) PCT No.: PCT/US2019/048185
§ 371 (c)(1),
(2) Date: Feb. 25, 2021

(87) PCT Pub. No.: WO2020/046837
PCT Pub. Date: Mar. 5, 2020

(65) Prior Publication Data
US 2021/0177926 A1    Jun. 17, 2021

Related U.S. Application Data

(60) Provisional application No. 62/723,420, filed on Aug. 27, 2018.

(51) Int. Cl.
| | | |
|---|---|---|
| *A61K 36/714* | (2006.01) | |
| *A61P 19/02* | (2006.01) | |
| *A61K 36/232* | (2006.01) | |
| *A61K 36/237* | (2006.01) | |
| *A61K 47/30* | (2006.01) | |

(52) U.S. Cl.
CPC .......... *A61K 36/714* (2013.01); *A61K 36/232* (2013.01); *A61K 36/237* (2013.01); *A61P 19/02* (2018.01); *A61K 47/30* (2013.01); *A61K 2236/331* (2013.01)

(58) Field of Classification Search
None
See application file for complete search history.

(56) References Cited

U.S. PATENT DOCUMENTS

2004/0142001 A1    7/2004    Kuok et al.

FOREIGN PATENT DOCUMENTS

| CN | 1626187 | A | | 6/2005 |
|---|---|---|---|---|
| CN | 2735955 | Y | | 10/2005 |
| CN | 101301452 | A | | 11/2008 |
| CN | 105902969 | A | * | 8/2016 |
| CN | 106075244 | A | | 11/2016 |
| CN | 107485651 | A | | 12/2017 |
| CN | 108143859 | A | | 6/2018 |

OTHER PUBLICATIONS

English translation, Abstract. CN 105902969A.*
CN105902969A machine translation (Dialog).*
CN105902969A paragraph [0022] Partial translation by United States Patent and Trademark Office Translations Service Center.*
Gao, X. et al. (Jan. 2006). National Excellent Course Chinese Medicine Project, Clinical Traditional Chinese Pharmacology, Shi Jiazhuang: Hebei Science &amp; Technology Press, Version 1, Section 1 Medicines for Eliminating Wind-Cold-Dampness, Chapter IV Antirheumatic Drugs, pp. 370-371, 374-375, 17 pages. (English Translation).
Guo, H. et al. (Dec. 31, 1988). "Clinical Treatise. Observation on Therapeutic Effects of Using Erwu Ointment Primarily for Treating Hyperplasia of Knee Joints and Calcaneus," Qinghai Medical Journal, No. 6, pp. 17-18, 8 pages. (English Translation).
International Preliminary Report on Patentability of the International Searching Authority dated Mar. 2, 2021 for PCT Patent Application No. PCT/US2019/48185, filed Aug. 26, 2019, 6 pages.
International Search Report and Written Opinion of the International Searching Authority dated Nov. 18, 2019 for PCT Patent Application No. PCT/US2019/48185, filed Aug. 26, 2019, 10 pages.
Mei, Q. (Oct. 2016). Handbook of Pharmacology and Clinical Application of Modern Traditional Chinese Medicine, China Traditional Chinese Medicine Press, 3rd Version, pp. 52-54, 559,561, 25 pages. (English Translation).
Ye, H. et al. (2016, e-pub. Jan. 9, 2016). "Identification of Inflammatory Factor TNFα Inhibitor from Medicinal Herbs," Experimental and Molecular Pathology 101(3):307-311.
Ye, H. et al. (2016, e-pub. Nov. 20, 2016). "Characterization of the Anti-Inflammation Mechanism for the AO Herbal Extract," Experimental and Molecular Pathology 101(3):341-345.

* cited by examiner

*Primary Examiner* — H. Sarah Park
(74) *Attorney, Agent, or Firm* — Morrison & Foerster LLP

(57) ABSTRACT

The present invention provides a composition of a mixture comprising *Radix Aconiti, Radix Aconiti Kusnezoffii, Rhizoma et Radix Notopterygii* and *Radix Angelicae Pubescentis*, and an herbal extract composition of a mixture comprising *Radix Aconiti, Radix Aconiti Kusnezoffii, Rhizoma et Radix Notopterygii* and *Radix Angelicae Pubescentis*. A method for preparing the herbal extract composition and a product by the method thereof is further provided by the present invention. The herbal extract composition is useful for alleviating pain and treating diseases such as rheumatoid arthritis (RA) or osteoarthritis (OA).

15 Claims, 3 Drawing Sheets

US 11,738,062 B2

HERBAL MEDICINE EXTRACTS AND USES AND METHODS OF PREPARATION THEREOF

CROSS-REFERENCE TO RELATED APPLICATION

This application is a national stage application under 35 U.S.C. § 371 of International Application No. PCT/US2019/048185, filed Aug. 26, 2019, which claims priority to U.S. Provisional Application No. 62/723,420, filed on Aug. 27, 2018, the contents of which are incorporated by reference herein in their entirety.

FIELD OF THE INVENTION

The present invention relates to the field of herbal medicine and herbal extract composition. In particular, the present invention relates to processed herbal compositions (such as an extract) comprising *Radix Aconiti, Radix Aconiti Kusnezoffii, Rhizoma et Radix Notopterygii* and *Radix Angelicae Pubescentis*, and their use in alleviating pain and treating diseases such as rheumatoid arthritis (RA), osteoarthritis (OA), sciatica, back pain, knee pain or pain caused by muscle strain.

BACKGROUND

In rheumatoid arthritis, the main presenting symptoms are pain, stiffness, swelling, and loss of function (Bennett J C. The etiology of rheumatoid arthritis. In Textbook of Rheumatology (Kelley W N, Harris E D, Ruddy S, Sledge C B, eds.) W B Saunders, Philadelphia pp 879-886, 1985). The multitude of drugs used in controlling such symptoms seems largely to reflect the fact that none is ideal. Although there have been many years of intense research into the biochemical, genetic, microbiological, and immunological aspects of rheumatoid arthritis, its pathogenesis is not completely understood, and none of the treatments clearly stop progression of joint destruction (Harris E D. Rheumatoid Arthritis: The clinical spectrum. In Textbook of Rheumatology (Kelley, *et al.*, eds.) W B Saunders, Philadelphia pp 915-990, 1985). Furthermore, currently available treatments involving broad immune suppression can lead to serious infections as well as concerns for lymphoma and other cancers.

Herbal medicine and nutritional supplements have long been widely applied by many cultures throughout the world to improve or maintain bodily functions. Traditional Chinese Medicine relies heavily on empirically-tested folk herbal medicines to treat human illnesses. Several herbs from Traditional Chinese Medicine possess anti-inflammatory or pain-alleviating effects, including *Radix Aconiti* (Root of Common Monkshood), *Radix Aconiti Kusnezoffii* (Kusnezoff Monkshood Root), *Rhizoma et Radix Notopterygii* (*Notopterygium* Root) and *Radix Angelicae Pubescentis* (Doubleteeth Pubescent *Angelica* Root). Nevertheless these herbs in their native forms are toxic and further processing is required to extract the active ingredients. Further complicating the issue is that different extraction methods will yield varying active ingredient profiles. The applicant has invented a novel way of preparing an herbal extract composition from these herbs for treating inflammatory or other diseases.

All references described herein are incorporated by reference in their entirety.

BRIEF SUMMARY OF THE INVENTION

In some aspects, the invention provides an herbal extract composition comprising an extract of a mixture comprising *Radix Aconiti, Radix Aconiti Kusnezoffii, Rhizoma et Radix Notopterygii* and *Radix Angelicae Pubescentis*.

In some embodiments, the invention provides an herbal extract composition comprising an extract of a mixture comprising *Radix Aconiti, Radix Aconiti Kusnezoffii, Rhizoma et Radix Notopterygii* and *Radix Angelicae Pubescentis*, wherein the mixture comprises about 10-70% (w) *Radix Aconiti*, about 10-70% (w) *Radix Aconiti Kusnezoffii*, about 10-70% (w) *Rhizoma et Radix Notopterygii* and about 10-70% (w) *Radix Angelicae Pubescentis*.

In some embodiments, the invention provides an herbal extract composition comprising an extract of a mixture comprising *Radix Aconiti, Radix Aconiti Kusnezoffii, Rhizoma et Radix Notopterygii* and *Radix Angelicae Pubescentis*, wherein the mixture comprises about 20-30% (w) *Radix Aconiti*, about 20-30% (w) *Radix Aconiti Kusnezoffii*, about 20-30% (w) *Rhizoma et Radix Notopterygii* and about 20-30% (w) *Radix Angelicae Pubescentis*.

In some embodiments according to any one of the herbal extract compositions described above, the composition further comprises a plant oil. In some embodiments, the composition comprises about 50-80% of plant oil by weight.

In some aspects, the invention provides a method for preparing an herbal extract composition from a mixture comprising *Radix Aconiti, Radix Aconiti Kusnezoffii, Rhizoma et Radix Notopterygii* and *Radix Angelicae Pubescentis*, the method comprising: i) adding a plant oil to the mixture comprising *Radix Aconiti, Radix Aconiti Kusnezoffii, Rhizoma et Radix Notopterygii* and *Radix Angelicae Pubescentis* to obtain a mixture in oil; ii) heating said mixture in oil at a temperature from about 60° C. to about 200° C., for about 5 minutes to about 10 hours; iii) collecting the liquid extract; and iv) optionally mixing the liquid extract with a polymer.

In some embodiments, the invention provides a method for preparing an herbal extract composition from a mixture comprising *Radix Aconiti, Radix Aconiti Kusnezoffii, Rhizoma et Radix Notopterygii* and *Radix Angelicae Pubescentis*, the method comprising: i) adding a plant oil to the mixture comprising *Radix Aconiti, Radix Aconiti Kusnezoffii, Rhizoma et Radix Notopterygii* and *Radix Angelicae Pubescentis* to obtain a mixture in oil; ii) heating said mixture in oil at a temperature from about 60° C. to about 200° C., for about 5 minutes to about 10 hours; iii) collecting the liquid extract; and iv) optionally mixing the liquid extract with a polymer; wherein the mixture comprises about 10-70% (w) *Radix Aconiti*, about 10-70% (w) *Radix Aconiti Kusnezoffii*, about 10-70% (w) *Rhizoma et Radix Notopterygii* and about 10-70% (w) *Radix Angelicae Pubescentis*.

In some embodiments, the invention provides a method for preparing an herbal extract composition from a mixture comprising *Radix Aconiti, Radix Aconiti Kusnezoffii, Rhizoma et Radix Notopterygii* and *Radix Angelicae Pubescentis*, the method comprising: i) adding a plant oil to the mixture comprising *Radix Aconiti, Radix Aconiti Kusnezoffii, Rhizoma et Radix Notopterygii* and *Radix Angelicae Pubescentis* to obtain a mixture in oil; ii) heating said mixture in oil at a temperature from about 60° C. to about 200° C., for about 5 minutes to about 10 hours; iii) collecting the liquid extract; and iv) optionally mixing the liquid extract with a polymer; wherein the mixture comprises about 20-30% (w) *Radix Aconiti*, about 20-30% (w) *Radix Aconiti Kusnezoffii*, about 20-30% (w) *Rhizoma et Radix Notopterygii* and about 20-30% (w) *Radix Angelicae Pubescentis*.

In some embodiments, the invention provides a method for preparing an herbal extract composition from a mixture comprising *Radix Aconiti, Radix Aconiti Kusnezoffii, Rhizoma et Radix Notopterygii and Radix Angelicae Pubescentis, the method comprising: i) adding a plant oil to the mixture comprising Radix Aconiti, Radix Aconiti Kusnezoffii, Rhizoma et Radix Notopterygii and Radix Angelicae Pubescentis to obtain a mixture in oil; ii) heating said mixture in oil at a temperature from about 60° C. to about 200° C., for about 5 minutes to about 10 hours; iii) collecting the liquid extract; and iv) optionally mixing the liquid extract with a polymer; wherein the smoke point of the plant oil is from about 120° C. to about 300° C. In some embodiments, the mixture in oil is heated to about 30-50% of the smoke point temperature of the plant oil. In some embodiments, the plant oil is refined, semi-refined or unrefined.

In some embodiments, provided is an herbal extract composition from a mixture comprising Radix Aconiti, Radix Aconiti Kusnezoffii, Rhizoma et Radix Notopterygii and Radix Angelicae Pubescentis, wherein the composition is prepared by i) adding a plant oil to the mixture comprising Radix Aconiti, Radix Aconiti Kusnezoffii, Rhizoma et Radix Notopterygii and Radix Angelicae Pubescentis to obtain a mixture in oil; ii) heating said mixture in oil at a temperature from about 60° C. to about 200° C., for about 5 minutes to about 10 hours; iii) collecting the liquid extract; and iv) optionally mixing the liquid extract with a polymer; wherein the plant oil is refined, semi-refined or unrefined. In some embodiments, the mixture comprises about 10-70% (w) Radix Aconiti, about 10-70% (w) Radix Aconiti Kusnezoffii, about 10-70% (w) Rhizoma et Radix Notopterygii and about 10-70% (w) Radix Angelicae Pubescentis. In some embodiments, the mixture comprises about 20-30% (w) Radix Aconiti, about 20-30% (w) Radix Aconiti Kusnezoffii, about 20-30% (w) Rhizoma et Radix Notopterygii and about 20-30% (w) Radix Angelicae Pubescentis. In some embodiments, the smoke point of the plant oil is from about 120° C. to about 300° C. In some embodiments, the mixture in oil is heated to about 30-50% of the smoke point temperature of the plant oil. In some embodiments, the plant oil is refined, semi-refined or unrefined.

In some embodiments according to any of the herbal extract composition described herein, the herbal extract composition further comprises an excipient. In some embodiments according to any of the herbal extract composition described herein, the excipient comprises one or more polymers. In some embodiments according to any of the herbal extract composition described herein, the herbal extract composition is in the form of a patch.

In another aspect, the invention provides a method of treating a disease of an individual, wherein the method comprises administering to the individual a therapeutically effective amount of an herbal extract composition comprising an extract of a mixture comprising Radix Aconiti, Radix Aconiti Kusnezoffii, Rhizoma et Radix Notopterygii and Radix Angelicae Pubescentis. In some embodiments, the method comprises administering to the individual a therapeutically effective amount of an herbal extract composition from a mixture comprising Radix Aconiti, Radix Aconiti Kusnezoffii, Rhizoma et Radix Notopterygii and Radix Angelicae Pubescentis, wherein the composition is prepared by i) adding a plant oil to the mixture comprising Radix Aconiti, Radix Aconiti Kusnezoffii, Rhizoma et Radix Notopterygii and Radix Angelicae Pubescentis to obtain a mixture in oil; ii) heating said mixture in oil at a temperature from about 60° C. to about 200° C., for about 5 minutes to about 10 hours; iii) collecting the liquid extract; and iv) optionally mixing the liquid extract with a polymer. In some embodiments, the mixture comprises about 10-70% (w) Radix Aconiti, about 10-70% (w) Radix Aconiti Kusnezoffii, about 10-70% (w) Rhizoma et Radix Notopterygii and about 10-70% (w) Radix Angelicae Pubescentis. In some embodiments, the mixture comprises about 20-30% (w) Radix Aconiti, about 20-30% (w) Radix Aconiti Kusnezoffii, about 20-30% (w) Rhizoma et Radix Notopterygii and about 20-30% (w) Radix Angelicae Pubescentis. In some embodiments, the smoke point of the plant oil is from about 120° C. to about 300° C. In some embodiments, the mixture in oil is heated to about 30-50% of the smoke point temperature of the plant oil. In some embodiments, the plant oil is refined, semi-refined or unrefined.

In some embodiments according to any one of the methods in treating a disease of an individual, the disease comprises an autoimmune or autoinflammatory disease. In some embodiments, the disease comprises an acute or chronic inflammatory disease. In some embodiments, the disease is selected from the group consisting of: rheumatoid arthritis (RA), osteoarthritis (OA), active polyarticular juvenile idiopathic arthritis (JIA), psoriatic arthritis. In some embodiments, the disease is rheumatoid arthritis. In some embodiments, the disease is selected from the group consisting of: sciatica, back pain, knee pain and pain caused by muscle strain. In some embodiments, the herbal extract composition is administered transdermally. In some embodiments, the individual is human.

In another aspect, the invention provides a composition comprising a mixture comprising Radix Aconiti, Radix Aconiti Kusnezoffii, Rhizoma et Radix Notopterygii and Radix Angelicae Pubescentis. In some embodiments, the composition comprises a mixture comprising about 10-70% (w) Radix Aconiti, about 10-70% (w) Radix Aconiti Kusnezoffii, about 10-70% (w) Rhizoma et Radix Notopterygii and about 10-70% (w) Radix Angelicae Pubescentis. In some embodiments, the composition comprises a mixture comprising about 20-30% (w) Radix Aconiti, about 20-30% (w) Radix Aconiti Kusnezoffii, about 20-30% (w) Rhizoma et Radix Notopterygii and about 20-30% (w) Radix Angelicae Pubescentis.

DETAILED DESCRIPTION OF THE INVENTION

Figure 1:
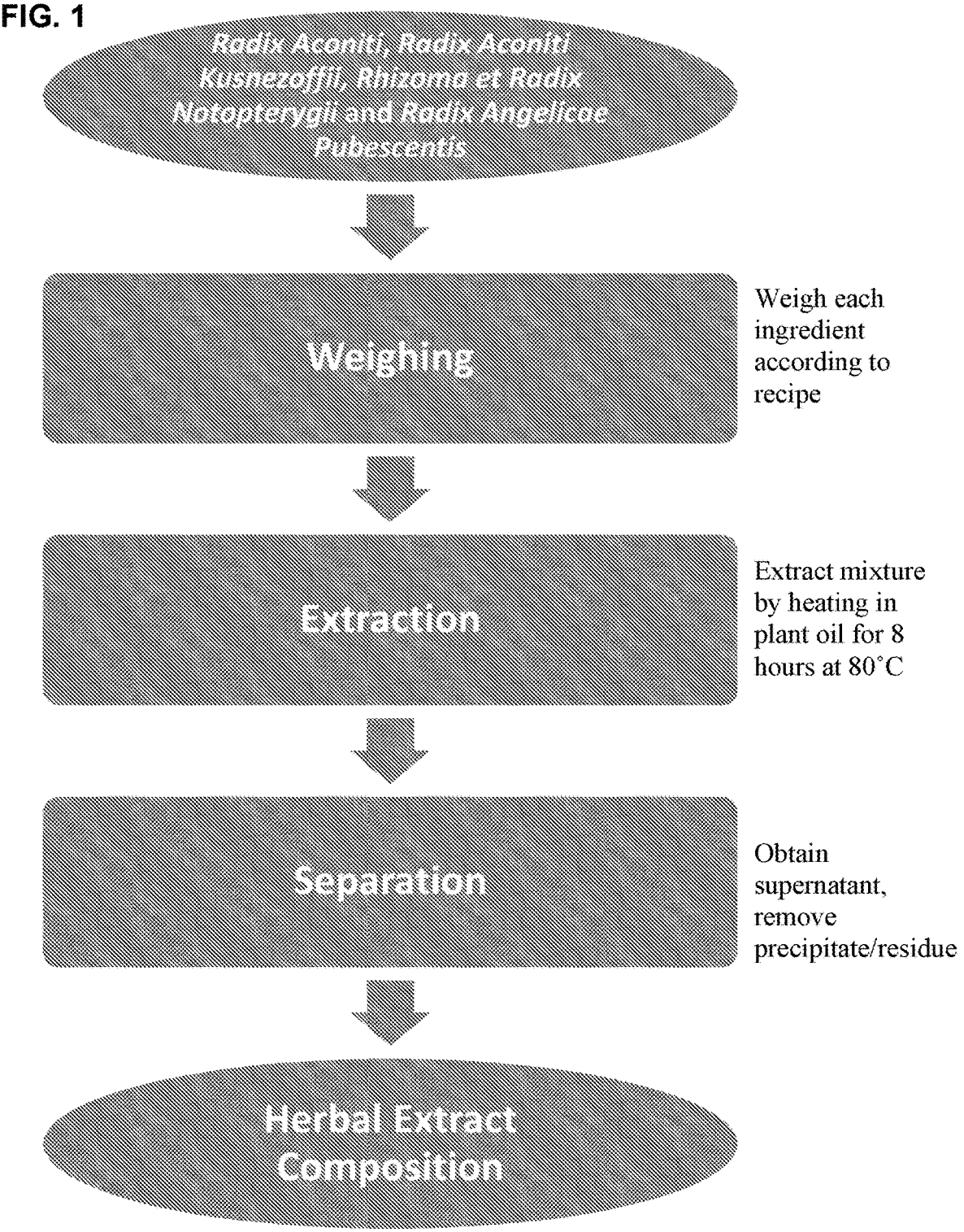
FIG. 1 shows a schematic flow chart of an exemplary embodiment of a method for preparing an herbal extract composition comprising an extract from a mixture of Radix Aconiti, Radix Aconiti Kusnezoffii, Rhizoma et Radix Notopterygii and Radix Angelicae Pubescentis.

The present invention provides an herbal extraction composition from a mixture of herbs. The mixture of herbs can comprise *Radix Aconiti, Radix Aconiti Kusnezoffii, Rhizoma et Radix Notopterygii* and *Radix Angelicae Pubescentis*. The present invention also provides methods for preparing an herbal extract composition from a mixture of herbs, where the method comprises steps of heating the mixture of herbs in a plant oil and collecting the liquid extract formulated in the plant oil. In some embodiments, the method can additionally include the step of mixing the liquid extract with a polymer. The herbal extract composition is surprisingly effective in alleviating pain or treating an inflammatory disease (e.g. rheumatoid arthritis) of an individual. In some examples, the herbal extract composition is provided in the form of an adhesive patch, to be applied to the area in need.

Definitions

For purposes of interpreting this specification, the following definitions will apply and whenever appropriate, terms used in the singular will also include the plural and vice versa. In the event that any definition set forth below conflicts with any document incorporated herein by reference, the definition set forth shall control.

As used herein, "treatment" is an approach for obtaining beneficial or desired clinical results. "Treatment" as used herein, covers any administration or application of a therapeutic for disease in an individual, including a human. For purposes of this invention, beneficial or desired clinical results include, but are not limited to, any one or more of: alleviation of one or more symptoms (e.g. pain) of a disease, reducing one or more symptoms (e.g. pain) of a disease, diminishment of extent of disease, preventing or delaying recurrence of disease, delaying or slowing of disease progression, amelioration of the disease state, inhibiting the disease or progression of the disease, or arresting its development. Also encompassed by "treatment" is a reduction of pathological consequence of a disease. The methods of the invention contemplate any one or more of these aspects of treatment. In the context of inflammatory disease, the term "treating" includes any or all of: inhibiting the progression of inflammation, lessening of overall inflammation and ameliorating one or more symptoms associated with the disease, including pain.

"Therapeutically effective amount" or "effective amount" in the present invention refers to an amount of the herbal extract composition, or the pharmaceutical composition sufficient to improve the condition of the individual in need thereof.

For any of the structural and functional characteristics described herein, methods of determining these characteristics are known in the art.

It is understood that aspects and embodiments of the invention described herein include "comprising," "consisting," and "consisting essentially of" aspects and embodiments.

Reference to "about" a value or parameter herein includes (and describes) variations that are directed to that value or parameter per se. For example, description referring to "about X" includes description of "X".

The term "about" as used herein refers to the usual error range for the respective value readily known to the skilled person in this technical field. Reference to "about" a value or parameter herein includes (and describes) embodiments that are directed to that value or parameter per se.

The term "about X-Y" used herein has the same meaning as "about X to about Y."

As used herein and in the appended claims, the singular forms "a," "an," "or," and "the" include plural referents unless the context clearly dictates otherwise.

Unless otherwise noted, technical terms are used according to conventional usage.

Herbal Mixture Composition and Herbal Extract Composition

*Radix Aconiti* is known as Common Monkshood Mother Root or Root of Common Monkshood by common name, and is also known under the Chinese name of "Chaun Wu". *Radix Aconiti* is the tuberous root of *Aconitum carmichaeli Debx*. of the family Ranuncculaceae. It is originally found in Sichuan, Yunnan, Shaanxi and Hunan provinces in China. *Radix Aconiti* is solid, brown in color and roughly triangular or conical in shape. When cross-sectioned, the inner area of the root is yellowish in color. *Radix Aconiti* in the raw form has a light pungent smell, and is spicy, bitter and benumbing in taste and can be highly toxic; while in some decocted forms it is slightly benumbing and without pungent smell.

*Radix Aconiti Kusnezoffii* (also known as *Radix Aconiti Agrestis*) is known as Kusnezoff Monkshood Root or Prepared Common Monkshood Daughter Root by common name, and is also known under the Chinese name of "Cao Wu." *Radix Aconiti Kusnezoffii* is the tuberous root of *Aconitum kusnezoffii Reichb*. It is originally found in the northeastern regions in China. In its native form, *Radix Aconiti Kusnezoffii* is solid, brown in color and is irregularly conical in shape. When cross-sectioned, the inner area of the root is gray or grayish white in color. *Radix Aconiti Kusnezoffii* in the raw form is pungent and bitter, and can be highly toxic.

*Rhizoma et Radix Notopterygii* is known as *Notopterygium* root by common name, and is also known under the Chinese name of "Qiang Huo." In medicine it mainly refers to the roots and rhizome of *Notopterygium incisum Tncisum Ting* ex *H. Chang* or *Notopterygium forbesii Boiss*. It is native to East Asia. In the raw form, the root is solid, brown in color and is elongated with circular ridges. In its raw form it has a fragrant smell, and is slightly bitter and pungent in taste. *Rhizoma et Radix Notopterygii* is normally removed from fibrous roots and soil before slicing, and is normally used raw.

*Radix Angelicae Pubescentis* is known as Pubescent Angelica Root by common name, and is also known under the Chinese name of "Du Huo." *Radix Angelicae Pubescentis* is the root of herbaceous plant *Angelica pubescens Maxim. f. biserrata* Shan et Yuan of family Umbelliferae. The root is slightly cylindrical, 10 to 30 cm long, with 2 to 3 or more branches in the lower part. The root head is dilated, conical shape in shape, 1.5 to 3 cm in diameter and with residue or depression left by stems and leaves on top. The surface is taupe or brown in color and is marked with longitudinal wrinkles and long ridged horizontal lenticels. It is originally found in Sichuan, Hubei and Anhui provinces in China. In its raw form it is fragrant, bitter and pungent in taste, and light benumbing. *Radix Angelicae Pubescentis* is usually used as unprocessed root.

In some embodiments, one or more of the roots of *Radix Aconiti, Radix Aconiti Kusnezoffii, Rhizoma et Radix Notopterygii* and *Radix Angelicae Pubescenti* being used are fresh. In some embodiments, one or more of the roots of *Radix Aconiti, Radix Aconiti Kusnezoffii, Rhizoma et Radix Notopterygii* and *Radix Angelicae Pubescenti* being used are dried.

In one aspect, provided is a composition comprising a mixture comprising *Radix Aconiti, Radix Aconiti Kusnezoffii, Rhizoma et Radix Notopterygii* and *Radix Angelicae*

Pubescentis (referred to as "herbal mixture" hereafter). Through certain extraction methods, an herbal extract composition can be derived from the herbal mixture. Thus in another aspect, provided is an herbal extract composition comprising an extract of a mixture comprising *Radix Aconiti*, *Radix Aconiti Kusnezoffii*, *Rhizoma et Radix Notopterygii* and *Radix Angelicae Pubescentis* (the "herbal mixture").

In some embodiments, the weight percentage of *Radix Aconiti* in the herbal mixture is about 1-97%. In some embodiments, the weight percentage of *Radix Aconiti* in the herbal mixture is about 5-85%. In some embodiments, the weight percentage of *Radix Aconiti* in the herbal mixture is about 10-70%. In some embodiments, the weight percentage of *Radix Aconiti* in the herbal mixture is about 10-70%. In some embodiments, the percentage by weight of *Radix Aconiti* in the herbal mixture is any one of: about 1-97%, about 5-85%, about 10-70%, about 15-55%, about 20-40%, or about 20-30%. In some embodiments, the percentage by weight of *Radix Aconiti* in the herbal mixture is any one of: about 8-15%, about 10-20%, about 60-70%, about 55-70%, or about 55-80%. In some embodiments, the percentage by weight of *Radix Aconiti* in the herbal mixture is about any one of: about 1-5%, about 5-10%, about 10-15%, about 15-20%, about 20-25%, about 25-30%, about 30-35%, about 35-40%, about 40-45%, about 45-50%, about 50-55%, about 55-60%, about 60-65%, about 65-70%, about 70-75%, about 75-80%, about 80-85%, about 85-90%, about 90-95%, or about 95-97%. In some embodiments, the percentage by weight of *Radix Aconiti* in the herbal mixture is about any one of: about 1%, about 5%, about 10%, about 12.5%, about 15%, about 20%, about 25%, about 30%, about 35%, about 40%, about 45% about 50%, about 55%, about 60%, about 62.5%, about 65%, about 70%, about 75%, about 80%, about 85%, about 90%, about 95% or about 97%.

In some embodiments, the weight percentage of *Radix Aconiti Kusnezoffii* in the herbal mixture is about 1-97%. In some embodiments, the weight percentage of *Radix Aconiti Kusnezoffii* in the herbal mixture is about 5-85%. In some embodiments, the weight percentage of *Radix Aconiti Kusnezoffii* in the herbal mixture is about 10-70%. In some embodiments, the weight percentage of *Radix Aconiti Kusnezoffii* in the herbal mixture is about 10-70%. In some embodiments, the percentage by weight of *Radix Aconiti Kusnezoffii* in the herbal mixture is any one of: about 1-97%, about 5-85%, about 10-70%, about 15-55%, about 20-40%, or about 20-30%. In some embodiments, the percentage by weight of *Radix Aconiti Kusnezoffii* in the herbal mixture is any one of: about 8-15%, about 10-20%, about 60-70%, about 55-70%, or about 55-80%. In some embodiments, the percentage by weight of *Radix Aconiti Kusnezoffii* in the herbal mixture is about any one of: about 1-5%, about 5-10%, about 10-15%, about 15-20%, about 20-25%, about 25-30%, about 30-35%, about 35-40%, about 40-45%, about 45-50%, about 50-55%, about 55-60%, about 60-65%, about 65-70%, about 70-75%, about 75-80%, about 80-85%, about 85-90%, about 90-95%, or about 95-97%. In some embodiments, the percentage by weight of *Radix Aconiti Kusnezoffii* in the herbal mixture is about any one of: about 1%, about 5%, about 10%, about 12.5%, about 15%, about 20%, about 25%, about 30%, about 35%, about 40%, about 45% about 50%, about 55%, about 60%, about 62.5%, about 65%, about 70%, about 75%, about 80%, about 85%, about 90%, about 95% or about 97%.

In some embodiments, the weight percentage of *Rhizoma et Radix Notopterygii* in the herbal mixture is about 1-97%. In some embodiments, the weight percentage of *Rhizoma et Radix Notopterygii* in the herbal mixture is about 5-85%. In some embodiments, the weight percentage of *Rhizoma et Radix Notopterygii* in the herbal mixture is about 10-70%. In some embodiments, the weight percentage of *Rhizoma et Radix Notopterygii* in the herbal mixture is about 10-70%. In some embodiments, the percentage by weight of *Rhizoma et Radix Notopterygii* in the herbal mixture is any one of: about 1-97%, about 5-85%, about 10-70%, about 15-55%, about 20-40%, or about 20-30%. In some embodiments, the percentage by weight of *Rhizoma et Radix Notopterygii* in the herbal mixture is any one of: about 8-15%, about 10-20%, about 60-70%, about 55-70%, or about 55-80%. In some embodiments, the percentage by weight of *Rhizoma et Radix Notopterygii* in the herbal mixture is about any one of: about 1-5%, about 5-10%, about 10-15%, about 15-20%, about 20-25%, about 25-30%, about 30-35%, about 35-40%, about 40-45%, about 45-50%, about 50-55%, about 55-60%, about 60-65%, about 65-70%, about 70-75%, about 75-80%, about 80-85%, about 85-90%, about 90-95%, or about 95-97%. In some embodiments, the percentage by weight of *Rhizoma et Radix Notopterygii* in the herbal mixture is about any one of: about 1%, about 5%, about 10%, about 12.5%, about 15%, about 20%, about 25%, about 30%, about 35%, about 40%, about 45% about 50%, about 55%, about 60%, about 62.5%, about 65%, about 70%, about 75%, about 80%, about 85%, about 90%, about 95% or about 97%.

In some embodiments, the weight percentage of *Radix Angelicae Pubescentis* in the herbal mixture is about 1-97%. In some embodiments, the weight percentage of *Radix Angelicae Pubescentis* in the herbal mixture is about 5-85%. In some embodiments, the weight percentage of *Radix Angelicae Pubescentis* in the herbal mixture is about 10-70%. In some embodiments, the weight percentage of *Radix Angelicae Pubescentis* in the herbal mixture is about 10-70%. In some embodiments, the percentage by weight of *Radix Angelicae Pubescentis* in the herbal mixture is any one of: about 1-97%, about 5-85%, about 10-70%, about 15-55%, about 20-40%, or about 20-30%. In some embodiments, the percentage by weight of *Radix Angelicae Pubescentis* in the herbal mixture is any one of: about 8-15%, about 10-20%, about 60-70%, about 55-70%, or about 55-80%. In some embodiments, the percentage by weight of *Radix Angelicae Pubescentis* in the herbal mixture is about any one of: about 1-5%, about 5-10%, about 10-15%, about 15-20%, about 20-25%, about 25-30%, about 30-35%, about 35-40%, about 40-45%, about 45-50%, about 50-55%, about 55-60%, about 60-65%, about 65-70%, about 70-75%, about 75-80%, about 80-85%, about 85-90%, about 90-95%, or about 95-97%. In some embodiments, the percentage by weight of *Radix Angelicae Pubescentis* in the herbal mixture is about any one of: about 1%, about 5%, about 10%, about 12.5%, about 15%, about 20%, about 25%, about 30%, about 35%, about 40%, about 45% about 50%, about 55%, about 60%, about 62.5%, about 65%, about 70%, about 75%, about 80%, about 85%, about 90%, about 95% or about 97%.

The present application contemplates an herbal mixture comprising *Radix Aconiti*, *Radix Aconiti Kusnezoffii*, *Rhizoma et Radix Notopterygii* and *Radix Angelicae Pubescentis*, each at any of the amounts or weight percentages described in the above paragraphs.

In some embodiments, the herbal mixture comprises *Radix Aconiti*, *Radix Aconiti Kusnezoffii*, *Rhizoma et Radix Notopterygii* and *Radix Angelicae Pubescentis* wherein the ratio by weight of *Radix Aconiti* to *Radix Aconiti Kusnezoffii* is any one of: about 20:1, about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, about 1:10 or about 1:20. In some embodiments, the ratio by weight of *Radix Aconiti* to *Radix Aconiti Kusnezoffii* is about any one of: about 5:1, about 1:1 or about 1:5.

In some embodiments, the herbal mixture comprises *Radix Aconiti, Radix Aconiti Kusnezoffii, Rhizoma et Radix Notopterygii* and *Radix Angelicae Pubescentis* wherein the ratio by weight of *Radix Aconiti* to *Rhizoma et Radix Notopterygii* is any one of: about 20:1, about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, about 1:10 or about 1:20. In some embodiments, the ratio by weight of *Radix Aconiti* to *Rhizoma et Radix Notopterygii* is about any one of: about 5:1, about 1:1 or about 1:5.

In some embodiments, the herbal mixture comprises *Radix Aconiti, Radix Aconiti Kusnezoffii, Rhizoma et Radix Notopterygii* and *Radix Angelicae Pubescentis* wherein the ratio by weight of *Radix Aconiti* to *Radix Angelicae Pubescentis* is any one of: about 20:1, about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, about 1:10 or about 1:20. In some embodiments, the ratio by weight of *Radix Aconiti* to *Radix Angelicae Pubescentis* is about any one of: about 5:1, about 1:1 or about 1:5.

In some embodiments, the herbal mixture comprises *Radix Aconiti, Radix Aconiti Kusnezoffii, Rhizoma et Radix Notopterygii* and *Radix Angelicae Pubescentis* wherein the ratio by weight of *Radix Aconiti Kusnezoffii* to *Rhizoma et Radix Notopterygii* is any one of: about 20:1, about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, about 1:10 or about 1:20. In some embodiments, the ratio by weight of *Radix Aconiti Kusnezoffii* to *Rhizoma et Radix Notopterygii* is about any one of: about 5:1, about 1:1 or about 1:5.

In some embodiments, the herbal mixture comprises *Radix Aconiti, Radix Aconiti Kusnezoffii, Rhizoma et Radix Notopterygii* and *Radix Angelicae Pubescentis* wherein the ratio by weight of *Radix Aconiti Kusnezoffii* to *Radix Angelicae Pubescentis* is any one of: about 20:1, about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, about 1:10 or about 1:20. In some embodiments, the ratio by weight of *Radix Aconiti Kusnezoffii* to *Radix Angelicae Pubescentis* is about any one of: about 5:1, about 1:1 or about 1:5.

In some embodiments, the herbal mixture comprises *Radix Aconiti, Radix Aconiti Kusnezoffii, Rhizoma et Radix Notopterygii* and *Radix Angelicae Pubescentis* wherein the ratio by weight of *Rhizoma et Radix Notopterygii* to *Radix Angelicae Pubescentis* is any one of: about 20:1, about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, about 1:10 or about 1:20. In some embodiments, the ratio by weight of *Rhizoma et Radix Notopterygii* to *Radix Angelicae Pubescentis* is about any one of: about 5:1, about 1:1 or about 1:5.

In some embodiments, the herbal mixture comprises *Radix Aconiti, Radix Aconiti Kusnezoffii, Rhizoma et Radix Notopterygii* and *Radix Angelicae Pubescentis* wherein the ratio by weight of *Radix Aconiti, Radix Aconiti Kusnezoffii, Rhizoma et Radix Notopterygii* and *Radix Angelicae Pubescentis* is about any one of: about 1:1:1:2, about 1:1:2:1, about 1:2:1:1, about 2:1:1:1, about 1:1:2:2, about 1:2:1:2, about 1:2:2:1, about 2:1:2:1, about 2:2:1:1, about 2:1:1:2, about 1:2:2:2, about 2:1:2:2, about 2:2:1:2, about 2:2:2:1, about 1:1:1:3, about 1:1:3:1, about 1:3:1:1, about 3:1:1:1, about 1:1:3:3, about 1:3:1:3, about 1:3:3:1, about 3:1:3:1, about 3:3:1:1, about 3:1:1:3, about 1:3:3:3, about 3:1:3:3, about 3:3:1:3, about 3:3:3:1, about 1:1:1:4, about 1:1:4:1, about 1:4:1:1, about 4:1:1:1, about 1:1:4:4, about 1:4:1:4, about 1:4:4:1, about 4:1:4:1, about 4:4:1:1, about 4:1:1:4, about 1:4:4:4, about 4:1:4:4, about 4:4:1:4, about 4:4:4:1, about 1:1:1:5, about 1:1:5:1, about 1:5:1:1, about 5:1:1:1, about 1:1:5:5, about 1:5:1:5, about 1:5:5:1, about 5:1:5:1, about 5:5:1:1, about 5:1:1:5, about 1:5:5:5, about 5:1:5:5, about 5:5:1:5, or about 5:5:5:1.

In one aspect, provided is an herbal extract composition comprising an extract of a mixture comprising *Radix Aconiti, Radix Aconiti Kusnezoffii, Rhizoma et Radix Notopterygii* and *Radix Angelicae Pubescentis*. In some embodiments, the mixture comprises about 1-97% (w) *Radix Aconiti*, about 1-97% (w) *Radix Aconiti Kusnezoffii*, about 1-97% (w) *Rhizoma et Radix Notopterygii* and about 1-97% (w) *Radix Angelicae Pubescentis*. In some embodiments, the mixture comprises about 5-85% (w) *Radix Aconiti*, about 5-85% (w) *Radix Aconiti Kusnezoffii*, about 5-85% (w) *Rhizoma et Radix Notopterygii* and about 5-85% (w) *Radix Angelicae Pubescentis*. In some embodiments, the mixture comprises about 10-70% (w) *Radix Aconiti*, about 10-70% (w) *Radix Aconiti Kusnezoffii*, about 10-70% (w) *Rhizoma et Radix Notopterygii* and about 10-70% (w) *Radix Angelicae Pubescentis*. In some embodiments, the mixture comprises about 15-55% (w) *Radix Aconiti*, about 15-55% (w) *Radix Aconiti Kusnezoffii*, about 15-55% (w) *Rhizoma et Radix Notopterygii* and about 15-55% (w) *Radix Angelicae Pubescentis*. In some embodiments, the mixture comprises about 20-40% (w) *Radix Aconiti*, about 20-40% (w) *Radix Aconiti Kusnezoffii*, about 20-40% (w) *Rhizoma et Radix Notopterygii* and about 20-40% (w) *Radix Angelicae Pubescentis*. In some embodiments, the mixture comprises about 20-30% (w) *Radix Aconiti*, about 20-30% (w) *Radix Aconiti Kusnezoffii*, about 20-30% (w) *Rhizoma et Radix Notopterygii* and about 20-30% (w) *Radix Angelicae Pubescentis*. In some embodiments, the mixture comprises about 25% (w) *Radix Aconiti*, about 25% (w) *Radix Aconiti Kusnezoffii*, about 25% (w) *Rhizoma et Radix Notopterygii* and about 25% (w) *Radix Angelicae Pubescentis*.

In some embodiments, the mixture comprises about 55-80% (w) *Radix Aconiti*, about 8-15% (w) *Radix Aconiti Kusnezoffii*, about 8-15% (w) *Rhizoma et Radix Notopterygii* and about 8-15% (w) *Radix Angelicae Pubescentis*. In some embodiments, the mixture comprises about 55-70% (w) *Radix Aconiti*, about 10-15% (w) *Radix Aconiti Kusnezoffii*, about 10-15% (w) *Rhizoma et Radix Notopterygii* and about 10-15% (w) *Radix Angelicae Pubescentis*. In some embodiments, the mixture comprises about 60-70% (w) *Radix Aconiti*, about 10-20% (w) *Radix Aconiti Kusnezoffii*, about 10-20% (w) *Rhizoma et Radix Notopterygii* and about 10-20% (w) *Radix Angelicae Pubescentis*. In some embodiments, the mixture comprises about 60-65% (w) *Radix Aconiti*, about 10-15% (w) *Radix Aconiti Kusnezoffii*, about 10-15% (w) *Rhizoma et Radix Notopterygii* and about 10-15% (w) *Radix Angelicae Pubescentis*. In some embodiments, the mixture comprises about 62.5% (w) *Radix Aconiti*, about 12.5% (w) *Radix Aconiti Kusnezoffii*, about 12.5% (w) *Rhizoma et Radix Notopterygii* and about 12.5% (w) *Radix Angelicae Pubescentis*.

In some embodiments, the mixture comprises about 8-15% (w) *Radix Aconiti*, about 55-80% (w) *Radix Aconiti Kusnezoffii*, about 8-15% (w) *Rhizoma et Radix Notopterygii* and about 8-15% (w) *Radix Angelicae Pubescentis*. In some embodiments, the mixture comprises about 10-15% (w) *Radix Aconiti*, about 55-70% (w) *Radix Aconiti Kusnezoffii*, about 10-15% (w) *Rhizoma et Radix Notopterygii* and about 10-15% (w) *Radix Angelicae Pubescentis*. In some embodiments, the mixture comprises about 10-20% (w) *Radix Aconiti*, about 60-70% (w) *Radix Aconiti Kusnezoffii*, about 10-20% (w) *Rhizoma et Radix Notopterygii* and about 10-20% (w) *Radix Angelicae Pubescentis*. In some embodiments, the mixture comprises about 10-15% (w) *Radix Aconiti*, about 60-65% (w) *Radix Aconiti Kusnezoffii*, about 10-15% (w) *Rhizoma et Radix Notopterygii* and about 10-15% (w) *Radix Angelicae Pubescentis*. In some embodiments, the mixture comprises about 12.5% (w) *Radix Aconiti*, about 62.5% (w) *Radix Aconiti Kusnezoffii*, about 12.5% (w) *Rhizoma et Radix Notopterygii* and about 12.5% (w) *Radix Angelicae Pubescentis*.

In some embodiments, the mixture comprises about 8-15% (w) *Radix Aconiti*, about 8-15% (w) *Radix Aconiti Kusnezoffii*, about 55-80% (w) *Rhizoma et Radix Notopterygii* and about 8-15% (w) *Radix Angelicae Pubescentis*. In some embodiments, the mixture comprises about 10-15% (w) *Radix Aconiti*, about 10-15% (w) *Radix Aconiti Kusnezoffii*, about 55-70% (w) *Rhizoma et Radix Notopterygii* and about 10-15% (w) *Radix Angelicae Pubescentis*. In some embodiments, the mixture comprises about 10-20% (w) *Radix Aconiti*, about 10-20% (w) *Radix Aconiti Kusnezoffii*, about 60-70% (w) *Rhizoma et Radix Notopterygii* and about 10-20% (w) *Radix Angelicae Pubescentis*. In some embodiments, the mixture comprises about 10-15% (w) *Radix Aconiti*, about 10-15% (w) *Radix Aconiti Kusnezoffii*, about 60-65% (w) *Rhizoma et Radix Notopterygii* and about 10-15% (w) *Radix Angelicae Pubescentis*. In some embodiments, the mixture comprises about 12.5% (w) *Radix Aconiti*, about 12.5% (w) *Radix Aconiti Kusnezoffii*, about 62.5% (w) *Rhizoma et Radix Notopterygii* and about 12.5% (w) *Radix Angelicae Pubescentis*.

In some embodiments, the mixture comprises about 8-15% (w) *Radix Aconiti*, about 8-15% (w) *Radix Aconiti Kusnezoffii*, about 8-15% (w) *Rhizoma et Radix Notopterygii* and about 55-80% (w) *Radix Angelicae Pubescentis*. In some embodiments, the mixture comprises about 10-15% (w) *Radix Aconiti*, about 10-15% (w) *Radix Aconiti Kusnezoffii*, about 10-15% (w) *Rhizoma et Radix Notopterygii* and about 55-70% (w) *Radix Angelicae Pubescentis*. In some embodiments, the mixture comprises about 10-20% (w) *Radix Aconiti*, about 10-20% (w) *Radix Aconiti Kusnezoffii*, about 10-20% (w) *Rhizoma et Radix Notopterygii* and about 60-70% (w) *Radix Angelicae Pubescentis*. In some embodiments, the mixture comprises about 10-15% (w) *Radix Aconiti*, about 10-15% (w) *Radix Aconiti Kusnezoffii*, about 10-15% (w) *Rhizoma et Radix Notopterygii* and about 60-65% (w) *Radix Angelicae Pubescentis*. In some embodiments, the mixture comprises about 12.5% (w) *Radix Aconiti*, about 12.5% (w) *Radix Aconiti Kusnezoffii*, about 12.5% (w) *Rhizoma et Radix Notopterygii* and about 62.5% (w) *Radix Angelicae Pubescentis*.

In some embodiments, the mixture comprises about 1-5 kg of *Radix Aconiti*, about 1-5 kg of *Radix Aconiti Kusnezoffii*, about 1-5 kg of *Rhizoma et Radix Notopterygii* and about 1-5 kg of *Radix Angelicae Pubescentis* per 6 kg of the mixture. In some embodiments, the mixture comprises about 1-5 kg of *Radix Aconiti*, about 1-5 kg of *Radix Aconiti Kusnezoffii*, about 1-5 kg of *Rhizoma et Radix Notopterygii* and about 1-5 kg of *Radix Angelicae Pubescentis* per 8 kg of the mixture. In some embodiments, the mixture comprises about 1-5 kg of *Radix Aconiti*, about 1-5 kg of *Radix Aconiti Kusnezoffii*, about 1-5 kg of *Rhizoma et Radix Notopterygii* and about 1-5 kg of *Radix Angelicae Pubescentis* per 12 kg of the mixture. In some embodiments, the mixture comprises about 1-5 kg of *Radix Aconiti*, about 1-5 kg of *Radix Aconiti Kusnezoffii*, about 1-5 kg of *Rhizoma et Radix Notopterygii* and about 1-5 kg of *Radix Angelicae Pubescentis* per 16 kg of the mixture. In some embodiments, the mixture comprises about 1 kg of *Radix Aconiti*, about 1 kg of *Radix Aconiti Kusnezoffii*, about 1 kg of *Rhizoma et Radix Notopterygii* and about 1 kg of *Radix Angelicae Pubescentis* per 4 kg of the mixture. In some embodiments, the mixture comprises about 5 kg of *Radix Aconiti*, about 1 kg of *Radix Aconiti Kusnezoffii*, about 1 kg of *Rhizoma et Radix Notopterygii* and about 1 kg of *Radix Angelicae Pubescentis* per 8 kg of the mixture. In some embodiments, the mixture comprises about 1 kg of *Radix Aconiti*, about 5 kg of *Radix Aconiti Kusnezoffii*, about 1 kg of *Rhizoma et Radix Notopterygii* and about 1 kg of *Radix Angelicae Pubescentis* per 8 kg of the mixture. In some embodiments, the mixture comprises about 1 kg of *Radix Aconiti*, about 1 kg of *Radix Aconiti Kusnezoffii*, about 5 kg of *Rhizoma et Radix Notopterygii* and about 1 kg of *Radix Angelicae Pubescentis* per 8 kg of the mixture. In some embodiments, the mixture comprises about 1 kg of *Radix Aconiti*, about 1 kg of *Radix Aconiti Kusnezoffii*, about 1 kg of *Rhizoma et Radix Notopterygii* and about 5 kg of *Radix Angelicae Pubescentis* per 8 kg of the mixture.

Herbal Extract Composition and Method of Preparation

Also provided herein are methods for preparing an herbal extract composition from a mixture comprising *Radix Aconiti, Radix Aconiti Kusnezoffii, Rhizoma et Radix Notopterygii* and *Radix Angelicae Pubescentis*, the method comprising: i) adding a plant oil to an herbal mixture to obtain a mixture in oil; ii) heating said mixture in oil at a temperature from about 60° C. to about 200° C., for about 5 minutes to about 10 hours; and iii) collecting a liquid extract from the heated mixture; and iv) optionally mixing the liquid extract with a polymer.

In some embodiments, the ratio in weight (w/v) of the herbal mixture versus the volume of the plant oil is any one of about 20:1, about 15:1, about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, about 1:10, about 1:15, or about 1:20. In some embodiments, enough plant oil is added such that herbal mixture is completely submerged in the plant oil before extraction. In some embodiments, enough plant oil is added such that any solid residue remaining from the herbal mixture is completely submerged in the plant oil after extraction. In some embodiments, to each 1 kg of herbal mixture, any one of about 0.1 L, about 0.2 L, about 0.3 L, about 0.4 L, about 0.5 L, about 0.6 L, about 0.7 L, about 0.8 L, about 0.9 L, about 1 L, about 1.5 L, about 2 L, about 2.5 L, about 3 L, about 4 L, about 5 L, about 6 L, about 7 L, about 8 L, about 9 L or about 10 L of plant oil is added. In some embodiments, to each 1 kg of herbal mixture, any one of: about 0.1-0.25 L, about 0.25-0.5 L, about 0.5-0.75 L, about 0.75-1 L, about 1-2 L, about 2-3 L, about 3-4 L, about 4-5 L, about 5-6 L, about 6-7 L, about 7-8 L, about 8-9 L, or about 9-10 L of plant oil is added.

In some examples the herbal mixture may be processed before the extraction step. For example, the mixture can be broken down into smaller pieces and/or boiled before heating in plant oil, to improve extraction efficiency. In some embodiments, the mixture is crushed. In some embodiments, the mixture is ground. In some embodiments, the mixture is cut into smaller pieces. The herbal mixture can be broken down into smaller pieces by any one of: a kitchen knife, pestle and mortar, kitchen blender, fine powder mill grinder or an industrial grinder. In some embodiments, the method comprises grinding the herbal mixture into powder. In some embodiments, the method comprises grinding the herbal mixture into particles with average diameter of about 0.1-0.2 mm, about 0.2-0.3 mm, about 0.3-0.4 mm, about 0.4-0.5 mm, about 0.5-0.6 mm, about 0.6-0.7 mm, about 0.7-0.8 mm, about 0.8-0.9 mm, about 0.9-1.0 mm, about 1-2 mm, 2-5 mm, or about 5-10 mm. In some embodiments, the method comprises grinding the herbal mixture into particles with average diameter of about 5-10 µm, about 10-20 µm, about 20-30 µm, about 30-40 µm, about 40-50 µm, about 50-60 µm, about 60-70 µm, about 70-80 µm, about 80-90 µm, or about 90-100 µm. In some embodiments, the mixture is boiled. In some embodiments, the mixture is ground and boiled. In some embodiments, the mixture is ground and boiled in water. Accordingly, in some embodiments, the ground mixture is boiled for any one of: about 1 minute, about 2 minutes, about 3 minutes, about 4 minutes, about 5 minutes, about 6 minutes, about 7 minutes, about 8 minutes, about 9 minutes and about 10 minutes. In some embodiments, the herbal mixture is blanched (i.e. placed under cold running water after scalded in boiling water). The boiled or blanched herbal mixture can be air-dried or dried using an oven or a desiccator. In some embodiments, the herbal mixture is ground before boiling or blanching. In some embodiments, the herbal mixture is boiled or blanched before grinding.

The herbal mixture or processed herbal mixture can then be subjected to an extraction step involving heating in plant oil. In some embodiments, the method comprises heating the mixture in the plant oil at a temperature of any one of about 40-50° C., about 50-60° C., about 60-70° C., about 70-80° C., about 80-90° C., about 90-100° C., 100-110° C., about 110-120° C., about 120-130° C., about 130-140° C., about 140-150° C., about 150-160° C., about 160-170° C., about 170-180° C., about 180-190° C., or about 190-200° C. In some embodiments, the method comprises heating the mixture in the plant oil at a temperature of any one of about 40-60° C., about 60-80° C., about 80-100° C., 100-120° C., 120-140° C., 140-160° C., 160-180° C., or 180-200° C. In some embodiments, the method comprises heating the mixture in the plant oil at a temperature of about 60-200° C. In some embodiments, the method comprises heating the mixture in the plant oil at a temperature of about 75-150° C.

In some embodiments, the method comprises heating the mixture in the plant oil at a temperature of no more than about 200° C. In some embodiments, the method comprises heating the mixture in the plant oil at temperature no more than any one of about 70° C., about 80° C., about 90° C., about 100° C., about 110° C., about 120° C., about 130° C., about 140° C., about 150° C., about 160° C., about 170° C., about 180° C., about 190° C., about 200° C., about 210° C., about 220° C., about 230° C., about 240° C. or about 250° C.

In some embodiments, the method comprises heating the mixture in the plant oil at a temperature of no less than about 50° C. In some embodiments, the method comprises heating the mixture in the plant oil at temperature no less than any one of about 40° C., about 45° C., about 50° C., about 55° C., about 60° C., about 65° C., about 70° C., about 75° C., about 80° C., about 85° C., about 90° C., about 95° C., about 100° C., about 110° C., about 120° C., about 130° C., about 140° C. or about 150° C.

The plant oil used in extraction of the herbal mixture can affect the active ingredient profiles of the herbal extract composition. Certain oils, either alone or in combination of the active ingredients extracted, may also improve the medicinal value of the extract in treating certain diseases. Thus in some embodiments, the plant oil comprises one or more of: coconut oil, corn oil, cottonseed oil, olive oil, palm oil, peanut oil, rapeseed oil, safflower oil, sesame oil, soybean oil, sunflower oil, almond oil, beech nut oil, Brazil nut oil, cashewnut oil, flaxseed oil, hazelnut oil, macadamia oil, mongongo nut oil, pecan oil, pine nut oil, pistachio oil, walnut oil, pumpkin seed oil, grapefruit seed oil, lemon oil or orange oil. In some embodiments, the plant oil is refined, semi-refined or unrefined. In some embodiments, the plant oil comprises a blend of two or more oils, such as a blend of any one of 2, 3, 4, 5, 6, 7, or more oils described herein. In some embodiments, the plant oil consists of one type of oil.

Herbal extract may be extracted by heating in plant oil at a temperature that does not cause the plant oil to smoke or boil. In some embodiments, the method comprises heating the mixture in the plant oil at a temperature slightly below the smoke point of the plant oil. Thus in some embodiments, the method comprises heating the mixture in oil at a temperature about 1-5° C. or about 5-10° C. below the smoke point of the plant oil. In some embodiments, the method comprises heating the mixture in the plant oil at a temperature moderately below the smoke point of the plant oil. Thus in some embodiments, the method comprises heating the mixture in oil to about 50-70% of the smoke point temperature of the plant oil. For example, in some instances the method comprises heating the mixture in oil to about 100-140° C., when the smoke point of the plant oil is about 200° C. In some embodiments, the method comprises heating the mixture in the plant oil at a temperature substantially below the smoke point of the plant oil. Thus in some embodiments, the method comprises heating the mixture in oil to about 30-50% of the smoke point temperature of the plant oil. For example, in some instances the method comprises heating the mixture in oil to about 60-100° C., when the smoke point of the plant oil is about 200° C. In some embodiments, the method comprises heating the mixture in oil to any one of about 25-30%, 30-35%, about 35-40%, about 40-45%, about 45-50%, about 50-55%, about 55-60%, about 60-65%, about 65-70%, about 70-75%, about 75-80%, or about 80-90% of the smoke point temperature of the plant oil.

In some embodiments, the smoke point of the plant oil is from about 120° C. to about 300° C. In some embodiments, the smoke point of the plant oil is any one of about 120-130° C., about 130-140° C., about 140-150° C., about 150-160° C., about 160-170° C., about 170-180° C., about 180-190° C., about 190-200° C., about 200-210° C., about 210-220° C., about 220-230° C., about 230-240° C., about 240-250° C., about 250-260° C., about 260-270° C., about 270-280° C., about 280-290° C., or about 290-300° C. In some embodiments according to any one of the methods described above, the smoke point of the plant oil is any one of about 120-140° C., about 140-160° C., about 160-180° C., about 180-200° C., about 200-220° C., about 220-240° C., about 240-260° C., about 260-280° C., or about 280-300° C.

Absolute pressure is the zero-referenced pressure against perfect vacuum, and is equal to the sum of gauge pressure and the atmospheric pressure, where the atmospheric pressure can vary based on location and altitude. When heating or cooking in a pressure-adjustable device, the absolute pressure is thus the gauge pressure as shown on the device plus the surrounding atmospheric pressure. The absolute pressure under which an herbal medicine mixture is extracted may also affect the active ingredient profiles in the herbal extract composition. Thus, in some embodiments, the method comprises heating the mixture in oil at an absolute pressure that is lower than, equal to, or higher than atmospheric pressure at sea level. In some embodiments, the method comprises heating the mixture in oil at an absolute pressure of any one of: about 50-60 kPa, about 60-70 kPa, about 70-80 kPa, about 80-90 kPa, about 90-100 kPa, about 100-110 kPa, about 110-120 kPa, about 120-130 kPa, about 130-140 kPa, about 140-150 kPa, about 150-160 kPa, about 160-170 kPa, about 170-180 kPa, about 180-190 kPa, about 190-200 kPa, about 200-210 kPa, about 210-220 kPa, about 220-230 kPa, about 230-240 kPa, about 240-250 kPa, about 250-260 kPa, about 260-270 kPa, about 270-280 kPa, about 280-290 kPa, or about 290-300 kPa, about 300-310 kPa, about 310-320 kPa, about 320-330 kPa, about 330-340 kPa, about 340-350 kPa. For example, the mixture in oil is heated in a heating device with adjustable pressure, including but not limited to a pressure cooker.

In some embodiments, the method comprises heating the mixture in oil at an absolute pressure of no more than about 300 kPa. In some embodiments, the method comprises heating the mixture in the plant oil at temperature no more than any one of about 200 kPa, about 210 kPa, about 220 kPa, about 230 kPa, about 240 kPa, about 250 kPa, about 260 kPa, about 270 kPa, about 280 kPa, about 290 kPa, about 300 kPa, about 310 kPa, about 320 kPa, about 330 kPa, about 340 kPa or about 350 kPa.

In some embodiments, the method comprises heating the mixture in the plant oil at a temperature of no less than about 50 kPa. In some embodiments, the method comprises heating the mixture in the plant oil at temperature no less than any one of about 50 kPa, about 55 kPa, about 60 kPa, about 65 kPa, about 70 kPa, about 75 kPa, about 80 kPa, about 85 kPa, about 90 kPa, about 95 kPa, about 100 kPa, about 110 kPa, about 120 kPa, about 130 kPa, about 140 kPa or about 150 kPa.

The amount of time the herbs are heated in plant oil can influence the active ingredient profile, and can influence the relative amount of active ingredients extracted. Thus, in some embodiments, the method comprises heating the mixture for about 5 minutes to about 10 hours. In some embodiments, the method comprises heating the mixture for about 5 minutes to about 24 hours. In some embodiments according to any one of the methods described above, the method comprises heating the mixture for about 5-10 minutes, about 10-30 minutes, about 30-60 minutes, about 1-2 hours, about 2-4 hours, about 4-6 hours, about 6-8 hours, about 8-10 hours, about 10-12 hours, about 12-14 hours, about 14-16 hours, about 16-18 hours, about 18-20 hours, about 20-22 hours, or about 22-24 hours. In some embodiments according to any one of the methods described above, the method comprises heating the mixture for about 1-5 minutes, about 5-10 minutes, about 10-20 minutes, about 20-30 minutes, about 30-40 minutes, about 40-50 minutes, about 50-60 minutes, about 1-1.5 hours, about 1.5-2 hours, about 2-3 hours, about 3-4 hours, about 4-5 hours, about 5-6 hours, about 6-7 hours, about 7-8 hours, about 8-9 hours, about 9-10 hours, about 11-12 hours, about 12-13 hours, about 13-14 hours, about 14-15 hours, about 15-16 hours, about 16-17 hours, about 17-18 hours, about 18-19 hours, about 19-20 hours, about 20-21 hours, about 21-22 hours, about 22-23 hours, or about 23-24 hours. In some embodiments according to any one of the methods described above, the method comprises heating the mixture for any one of: about 2 minutes, about 5 minutes, about 10 minutes, about 20 minutes, about 30 minutes, about 40 minutes, about 50 minutes, about 1 hour, about 1.5 hours, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours. In some embodiments, the method comprises heating the mixture for at least about 1 hour (such as about any of 2, 3, 4, 5, 6, 7, 8, 9, 10 or more hours).

In some embodiments, the liquid extract is collected before the heated mixture is allowed to cool down. In some embodiments, the liquid extract is collected after the heated mixture is allowed to cool down. The liquid extract may be collected by physically excluding the solid residues. In some embodiments, the liquid extract is collected by decanting from the heated mixture. In some embodiments, the liquid extract is collected by passing the heated mixture through one or more constrictions. Many devices contain constrictions suitable for physically excluding the solid residues, including but not limited to sieves, strainers, filters, membranes or matrices of pores. Thus in some embodiments, the liquid extract is collected by passing the heated mixture through one or more sieves, strainers, filters, membranes or matrices of pores. In some embodiments, the diameters of the constrictions through which the liquid extract is passed through are about 5 µm, about 10 µm, about 15 µm, about 20 µm, about 25 µm, about 30 µm, about 40 µm, about 50 µm, about 60 µm, about 70 µm, about 80 µm, about 90 µm, about 100 µm, about 150 µm, about 200 µm, about 300 µm, about 400 µm, about 500 µm, about 600 µm, about 700 µm, about 800 µm, about 900 µm, 1 mm, about 2 mm, about 3 mm, about 4 mm, about 5 mm, or about 10 mm. In some embodiments, the liquid extract is passed through a series of constrictions of decreasing sizes. For example, the heated mixture can be passed through a series of strainers, starting from a 10 mm strainer, through a 1 mm strainer, a 100 µm strainer, and finally a 10 µm strainer, to allow efficient trapping of differently sized residues without clogging the strainers. In some embodiments, the diameter of the constriction used is at least about 1 µm, about 2 µm, about 3 µm, about 4 µm, about 5 µm, about 10 µm, about 20 µm, about 30 µm, about 40 µm, about 50 µm or about 100 µm smaller than the average diameter of the starting herbal mixture.

Different extraction parameters such as heating temperature, pressure, and duration of heating can affect the profile of active ingredients. After extraction, the liquid extract can comprise the extract of the herbal mixture formulated in the plant oil. Thus in some embodiments, the liquid extract comprises about 1-5%, about 5-10%, about 10-15%, about 15-20%, about 20-25%, about 25-30%, about 30-35%, about 35-40%, about 40-45%, about 45-50%, about 50-55%, about 55-60%, about 60-65%, about 65-70%, about 70-75%, about 75-80%, about 80-85%, about 85-90%, about 90-95%, or about 95-97% plant oil by weight.

In some embodiments, the method further comprises packing and sealing the herbal extract composition in a sterile container. In some embodiments, the container is a vial.

Further provided herein are herbal extract compositions prepared by any one of the methods described herein.

For example, in certain aspects, provided is an herbal extract composition comprising an extract of a mixture comprising *Radix Aconiti, Radix Aconiti Kusnezoffii, Rhizoma et Radix Notopterygii* and *Radix Angelicae Pubescenti*, wherein the herbal extract composition is prepared by a method comprising: i) adding a plant oil to the mixture comprising *Radix Aconiti, Radix Aconiti Kusnezoffii, Rhizoma et Radix Notopterygii* and *Radix Angelicae Pubescentis* to obtain a mixture in oil; ii) heating said mixture in oil at a temperature from about 60° C. to about 200° C., for about 5 minutes to about 10 hours; iii) collecting a liquid extract from the heated mixture; iv) optionally mixing the liquid extract with a polymer. In some embodiments, the herbal extract composition is prepared by any one of the methods described above.

Pharmaceutical Compositions

In some instances, the liquid herbal extract can be directly administered on the area in need of treatment, and optionally one or more sealing mechanisms (such as an adhesive bandage) can be applied on top to prevent spillage or evaporation. In other embodiments, the liquid can be further incorporated into other forms of pharmaceutical compositions.

In some embodiments, the composition further comprises an excipient. In some embodiments, an excipient is one or more of: mannose, mannitol, lactose, sucrose or cellulose. In some embodiments, the excipient is one or more polymers. In some embodiments, the polymer is one or more of: cellulose, hypromellose, acrylate, acrylic acid, lecithin, or polyisobutylene. In some embodiments, the composition is in the form of a paste. In some embodiments, the composition is in the form of an ointment. The paste and/or the ointment can be further incorporated into formats applicable for administration, such as into a patch.

The herbal extract compositions described above can be provided in formats applicable for transdermal administration. Polymers are the backbone of a transdermal drug delivery system. Systems for transdermal delivery can be fabricated as multilayered polymeric laminates in which a drug reservoir or a drug-polymer matrix is sandwiched between two polymeric layers: an outer impervious backing layer that prevents the loss of drug through the backing surface and an inner polymeric layer that functions as an adhesive and/or rate-controlling membrane. (Kandavilli et al. 2002, *Pharmaceutical Technology*, 26(5):62-81). In some embodiments, the herbal extract composition is in the form of a patch. A patch can include non-permanent adhesives to facilitate application in transdermal delivery. In some embodiments, the herbal extract composition is in the form of an adhesive patch. In some embodiments, the herbal extract composition is in the form of an adhesive polymer patch. In some embodiments, the liquid extract is incorporated into the patch. In some embodiments, the liquid extract is soaked onto a pad and incorporated into the patch. In some embodiments, the liquid extract is mixed with an excipient. In some embodiments, the liquid extract is mixed with a polymer to form an extract-polymer matrix in an adhesive polymer patch.

In some embodiments, there is provided a container comprising the herbal extract composition. In some embodiments, the container is opaque. In some embodiments, the container further comprises a label identifying the herbal extract composition. In some embodiments, the container is a vial. In some embodiments, the container is sterile. Thus in some embodiments, there is provided a sealed vial comprising the herbal extract composition.

Method of Treating Diseases

The herbal extract compositions described herein are useful for treating various diseases, such as autoimmune or autoimflammatory diseases. Some symptoms of diseases can include discomfort and/or pain in certain parts of the body. In one aspect, provided is a method of treating a disease of an individual, wherein the method comprises administering to the individual a therapeutically effective amount of an herbal extract composition of according to any one of the embodiments described above. In some embodiments, the disease is an autoimmune or autoinflammatory disease. In some embodiments, the disease is an acute or chronic inflammatory disease. In some embodiments, the disease is selected from the group consisting of: rheumatoid arthritis (RA), osteoarthritis (OA), active polyarticular juvenile idiopathic arthritis (JIA), and psoriatic arthritis. In some embodiments, the disease is rheumatoid arthritis. In some embodiments according to any one of the methods described above, the disease is selected from the group consisting of: sciatica, back pain, knee pain and pain caused by muscle strain. In some embodiments, the method of treatment has a systemic effect. In some embodiments according to any one of the methods described above, the method of treatment has a localized effect. For example, the herbal extract composition can be directly applied to the site of the disease, e.g. via transdermal delivery.

In some embodiments, the herbal extract composition is administered transdermally. In some embodiment, the method comprises the herbal extract composition in a dosage regimen of about 1 µL, about 5 µL, about 10 µL, about 25 µL, about 50 µL, about 75 µL, about 100 µL, about 200 µL, about 300 µL, about 400 µL, about 500 µL, about 600 µL, about 700 µL, about 800 µL, about 900 µL, about 1 mL, about 2 mL, about 3 mL, about 4 mL, about 5 mL, about 6 mL, about 7 mL, about 8 mL, about 9 mL, about 10 mL, or about 20 mL of the liquid extract per dose, where the herbal extract composition is prepared according to any exemplary embodiment described herein. In some embodiments, the method comprises administering the herbal extract composition at the frequency of 3 doses daily, two doses daily, one dose daily, one dose every two days, one dose every three days, one dose every four days, one dose every five days, one dose every seven days, one dose every ten days, one dose every two weeks, one dose every three weeks, or one dose per month. In some embodiments, the method comprises administering the herbal extract composition three times daily, twice daily, once daily, once every two days, once every three days, once every four days, once every five days, once every seven days, once every ten days, once every two weeks, once every three weeks, or once per month. In some embodiments, the method of treatment comprises about 1, about 2, about 3, about 4, about 5, about 6, about 7, about 8, about 9, about 10, about 11, about 12, about 15, about 20, about 25, about 30, about 35, about 40, about 45, about 50, about 60, about 70, about 80, about 90, about 100, about 125, about 150, about 175, about 200, about 250, about 300, or about 500 doses of the herbal extract composition. In some embodiments, the method of treatment is administered as needed.

In some embodiments according to any one of the methods described above, the individual is human. In some embodiments, the individual is a human female. In other embodiments, the individual is a human male. In some embodiments, the individual is between about 20 to about 100 years old. In further embodiments, the individual is between about 30 to about 90 years old. In some embodiments, the individual is between about 40 to about 90 years old. In some embodiments, the individual is between about 50 to between about 80 years old. In some embodiments, the individual is any one of between about 20 to about 30 years old, between about 30 to about 40 years old, between about 40 to about 50 years old, between about 50 to about 60 years old, between about 60 to about 70 years old, between about 70 to about 80 years old, between about 80 to about 90 years old, or between about 90 to about 100 years old.

Kits

Also provided are kits or articles of manufacture for use in treating individuals with a disease, such as an inflammatory disease. In some embodiments, the kit comprises an herbal extract composition described herein. In some embodiments, the kit comprises an herbal extract composition prepared according to methods described herein. In some embodiments, the kit comprises a composition of herbal mixture described herein. In some embodiments, the kit comprises the compositions described herein (e.g. a composition of herbal mixture, an herbal extract composition, or an herbal extract composition in the form of a patch) in suitable packaging. In some embodiments, the kit comprises a composition of herbal mixture described herein, in suitable packaging. In some embodiments, the kit comprises an herbal extract composition described herein, in suitable packaging. In some embodiments, the kit comprises an herbal extract composition in the form of a patch described herein, in suitable packaging. Suitable packaging materials are known in the art, and include, for example, vials (such as sealed vials), vessels, ampules, bottles, jars, flexible packaging (e.g., sealed Mylar or plastic bags), and the like. These articles of manufacture may further be sterilized and/or sealed. Further provided are the methods of producing the kits or articles of manufacture.

The invention also provides kits comprising components of the methods described herein and may further comprise instructions for performing said methods to treat an individual with rheumatoid arthritis. The kits described herein may further include other materials, including buffers, diluents, or plastic film protectors for patches, as well as package inserts with instructions for performing any methods described herein; e.g., instructions for treating an individual with arthritis disease or instructions for dosages and applications of the herbal extract composition or of the patches.

Other Embodiments

The present application in one aspect provides an herbal extract composition comprising an extract of a mixture comprising *Radix Aconiti*, *Radix Aconiti Kusnezoffii*, *Rhizoma et Radix Notopterygii* and *Radix Angelicae Pubescentis*. In some embodiments, there is provided an extract composition comprising an extract of a mixture comprising about 10-70% (w) *Radix Aconiti*, about 10-70% (w) *Radix Aconiti Kusnezoffii*, about 10-70% (w) *Rhizoma et Radix Notopterygii* and about 10-70% (w) *Radix Angelicae Pubescentis*. In some embodiments, the mixture comprises about 20-30% (w) *Radix Aconiti*, about 20-30% (w) *Radix Aconiti Kusnezoffii*, about 20-30% (w) *Rhizoma et Radix Notopterygii* and about 20-30% (w) *Radix Angelicae Pubescentis*. In some embodiments, the weight ratio of *Radix Aconiti*, *Radix Aconiti Kusnezoffii*, *Rhizoma et Radix Notopterygii* and *Radix Angelicae Pubescentis* in the mixture is any of: about 1:1:1:2, about 1:1:2:1, about 1:2:1:1, about 2:1:1:1, about 1:1:2:2, about 1:2:1:2, about 1:2:2:1, about 2:1:2:1, about 2:2:1:1, about 2:1:1:2, about 1:2:2:2, about 2:1:2:2, about 2:2:1:2, about 2:2:2:1, about 1:1:1:3, about 1:1:3:1, about 1:3:1:1, about 3:1:1:1, about 1:1:3:3, about 1:3:1:3, about 1:3:3:1, about 3:1:3:1, about 3:3:1:1, about 3:1:1:3, about 1:3:3:3, about 3:1:3:3, about 3:3:1:3, about 3:3:3:1, about 1:1:1:4, about 1:1:4:1, about 1:4:1:1, about 4:1:1:1, about 1:1:4:4, about 1:4:1:4, about 1:4:4:1, about 4:1:4:1, about 4:4:1:1, about 4:1:1:4, about 1:4:4:4, about 4:1:4:4, about 4:4:1:4, about 4:4:4:1, about 1:1:1:5, about 1:1:5:1, about 1:5:1:1, about 5:1:1:1, about 1:1:5:5, about 1:5:1:5, about 1:5:5:1, about 5:1:5:1, about 5:5:1:1, about 5:1:1:5, about 1:5:5:5, about 5:1:5:5, about 5:5:1:5, or about 5:5:5:1.

In some embodiments, the invention provides an herbal extract composition comprising an extract of a mixture comprising *Radix Aconiti*, *Radix Aconiti Kusnezoffii*, *Rhizoma et Radix Notopterygii* and *Radix Angelicae Pubescentis*, wherein the mixture comprises about 25% (w) *Radix Aconiti*, about 25% (w) *Radix Aconiti Kusnezoffii*, about 25% (w) *Rhizoma et Radix Notopterygii* and about 25% (w) *Radix Angelicae Pubescentis*.

In some embodiments, there is provided an herbal extract composition comprising an extract of a mixture comprising *Radix Aconiti*, *Radix Aconiti Kusnezoffii*, *Rhizoma et Radix Notopterygii* and *Radix Angelicae Pubescentis*, wherein the herbal extract composition further comprises plant oil. In some embodiments, the composition comprises about 50-60% of plant oil by weight.

In some embodiments, the invention provides an herbal extract composition comprising: 1) an extract of a mixture comprising *Radix Aconiti*, *Radix Aconiti Kusnezoffii*, *Rhizoma et Radix Notopterygii* and *Radix Angelicae Pubescentis*, wherein the mixture comprises about 25% (w) *Radix Aconiti*, about 25% (w) *Radix Aconiti Kusnezoffii*, about 25% (w) *Rhizoma et Radix Notopterygii* and about 25% (w) *Radix Angelicae Pubescentis*; and 2) plant oil. In some embodiments, the composition comprises about 50-60% of plant oil by weight.

In another aspect, there is provided a method of preparing an herbal extract composition from a mixture comprising *Radix Aconiti*, *Radix Aconiti Kusnezoffii*, *Rhizoma et Radix Notopterygii* and *Radix Angelicae Pubescentis*, the method comprising: i) adding a plant oil to the mixture comprising *Radix Aconiti*, *Radix Aconiti Kusnezoffii*, *Rhizoma et Radix Notopterygii* and *Radix Angelicae Pubescentis* to obtain a mixture in oil; ii) heating said mixture in oil at a temperature from about 60° C. to about 200° C., for about 5 minutes to about 10 hours; iii) collecting a liquid extract from the heated mixture; iv) optionally mixing the liquid extract with a polymer. In some embodiments, the mixture comprises about 10-70% (w) *Radix Aconiti*, about 10-70% (w) *Radix Aconiti Kusnezoffii*, about 10-70% (w) *Rhizoma et Radix Notopterygii* and about 10-70% (w) *Radix Angelicae Pubescentis*. In some embodiments, the mixture comprises about 20-30% (w) *Radix Aconiti*, about 20-30% (w) *Radix Aconiti Kusnezoffii*, about 20-30% (w) *Rhizoma et Radix Notopterygii* and about 20-30% (w) *Radix Angelicae Pubescentis*. In some embodiments, the weight ratio of *Radix Aconiti*, *Radix Aconiti Kusnezoffii*, *Rhizoma et Radix Notopterygii* and *Radix Angelicae Pubescentis* in the mixture is any of: about 1:1:1:2, about 1:1:2:1, about 1:2:1:1, about 2:1:1:1, about 1:1:2:2, about 1:2:1:2, about 1:2:2:1, about 2:1:2:1, about 2:2:1:1, about 2:1:1:2, about 1:2:2:2, about 2:1:2:2, about 2:2:1:2, about 2:2:2:1, about 1:1:1:3, about 1:1:3:1, about 1:3:1:1, about 3:1:1:1, about 1:1:3:3, about 1:3:1:3, about 1:3:3:1, about 3:1:3:1, about 3:3:1:1, about 3:1:1:3, about 1:3:3:3, about 3:1:3:3, about 3:3:1:3, about 3:3:3:1, about 1:1:1:4, about 1:1:4:1, about 1:4:1:1, about 4:1:1:1, about 1:1:4:4, about 1:4:1:4, about 1:4:4:1, about 4:1:4:1, about 4:4:1:1, about 4:1:1:4, about 1:4:4:4, about 4:1:4:4, about 4:4:1:4, about 4:4:4:1, about 1:1:1:5, about 1:1:5:1, about 1:5:1:1, about 5:1:1:1, about 1:1:5:5, about 1:5:1:5, about 1:5:5:1, about 5:1:5:1, about 5:5:1:1, about 5:1:1:5, about 1:5:5:5, about 5:1:5:5, about 5:5:1:5, or about 5:5:5:1.

In some embodiments, there is provided a method for preparing an herbal extract composition from a mixture comprising *Radix Aconiti, Radix Aconiti Kusnezoffii, Rhizoma et Radix Notopterygii* and *Radix Angelicae Pubescentis*, the method comprising: i) adding a plant oil to the mixture comprising *Radix Aconiti, Radix Aconiti Kusnezoffii, Rhizoma et Radix Notopterygii* and *Radix Angelicae Pubescentis* to obtain a mixture in oil; ii) heating said mixture in oil at a temperature from about 70° C. to about 80° C. for at least about an hour (for example about any of 2, 3, 4, or 5 hours); iii) collecting the liquid extract; and iv) optionally mixing the liquid extract with a polymer; wherein the smoke point of the plant oil is from about 210° C. to about 230° C. In some embodiments, about 1-2 L of plant oil is added per 1 kg of herbal mixture. In some embodiments, the mixture comprises about 10-70% (w) *Radix Aconiti*, about 10-70% (w) *Radix Aconiti Kusnezoffii*, about 10-70% (w) *Rhizoma et Radix Notopterygii* and about 10-70% (w) *Radix Angelicae Pubescentis*. In some embodiments, the mixture comprises about 20-30% (w) *Radix Aconiti*, about 20-30% (w) *Radix Aconiti Kusnezoffii*, about 20-30% (w) *Rhizoma et Radix Notopterygii* and about 20-30% (w) *Radix Angelicae Pubescentis*. In some embodiments, the weight ratio of *Radix Aconiti, Radix Aconiti Kusnezoffii, Rhizoma et Radix Notopterygii* and *Radix Angelicae Pubescentis* in the mixture is any of: about 1:1:1:2, about 1:1:2:1, about 1:2:1:1, about 2:1:1:1, about 1:1:2:2, about 1:2:1:2, about 1:2:2:1, about 2:1:2:1, about 2:2:1:1, about 2:1:1;2, about 1:2:2:2, about 2:1:2:2, about 2:2:1:2, about 2:2:2:1, about 1:1:1:3, about 1:1:3:1, about 1:3:1:1, about 3:1:1:1, about 1:1:3:3, about 1:3:1:3, about 1:3:3:1, about 3:1:3:1, about 3:3:1:1, about 3:1:1;3, about 1:3:3:3, about 3:1:3:3, about 3:3:1:3, about 3:3:3:1, about 1:1:1:4, about 1:1:4:1, about 1:4:1:1, about 4:1:1:1, about 1:1:4:4, about 1:4:1:4, about 1:4:4:1, about 4:1:4:1, about 4:4:1:1, about 4:1:1;4, about 1:4:4:4, about 4:1:4:4, about 4:4:1:4, about 4:4:4:1, about 1:1:1:5, about 1:1:5:1, about 1:5:1:1, about 5:1:1:1, about 1:1:5:5, about 1:5:1:5, about 1:5:5:1, about 5:1:5:1, about 5:5:1:1, about 1:1:5:5, about 1:5:1:5, about 1:5:5:1, about 5:1:5:1, about 5:5:1:1, about 5:1:1:5, about 1:5:5:5, about 5:1:5:5, about 5:5:1:5, or about 5:5:5:1.

In some embodiments, the invention provides a method for preparing an herbal extract composition from a mixture comprising *Radix Aconiti, Radix Aconiti Kusnezoffii, Rhizoma et Radix Notopterygii* and *Radix Angelicae Pubescentis*, the method comprising: i) adding a plant oil to the mixture comprising *Radix Aconiti, Radix Aconiti Kusnezoffii, Rhizoma et Radix Notopterygii* and *Radix Angelicae Pubescentis* to obtain a mixture in oil; ii) heating said mixture in oil at a temperature from about 70° C. to about 80° C., for at least an hour (for example about any of 2, 3, 4, or 5 hours); iii) collecting the liquid extract; and iv) optionally mixing the liquid extract with a polymer; wherein the ratio by weight of *Radix Aconiti, Radix Aconiti Kusnezoffii, Rhizoma et Radix Notopterygii* and *Radix Angelicae Pubescentis* is about 1:1:1:1, wherein about 1-2 L of plant oil is added per 1 kg of herbal mixture, and wherein the smoke point of the plant oil is from about 210° C. to about 230° C. In some embodiments, about 1-2 L of plant oil is added per 1 kg of herbal mixture.

Also provided herein are herbal extract compositions prepared by any of the methods described herein.

Also provided are methods of treating disease (such as rheumatoid arthritis) by administering any of the herbal extract composition described herein. For example, in some embodiments, the invention provides a method of treating rheumatoid arthritis of an individual, wherein the method comprises administering to the individual a therapeutically effective amount of an herbal extract composition comprising an extract of a mixture comprising *Radix Aconiti, Radix Aconiti Kusnezoffii, Rhizoma et Radix Notopterygii* and *Radix Angelicae Pubescentis*. In some embodiments, the method comprises administering to the individual a therapeutically effective amount of an herbal extract composition from a mixture comprising *Radix Aconiti, Radix Aconiti Kusnezoffii, Rhizoma et Radix Notopterygii* and *Radix Angelicae Pubescentis*, wherein the composition is prepared by i) adding a plant oil to the mixture comprising *Radix Aconiti, Radix Aconiti Kusnezoffii, Rhizoma et Radix Notopterygii* and *Radix Angelicae Pubescentis* to obtain a mixture in oil; ii) heating said mixture in oil at a temperature from about 70° C. to about 80° C., for at least about an hour (for example about any of 2, 3, 4, or 5 hours); iii) collecting the liquid extract; and iv) optionally mixing the liquid extract with a polymer; wherein the ratio by weight of *Radix Aconiti, Radix Aconiti Kusnezoffii, Rhizoma et Radix Notopterygii* and *Radix Angelicae Pubescentis* is about 1:1:1:1, wherein about 1-2 L of plant oil is added per 1 kg of herbal mixture, and wherein the smoke point of the plant oil is from about 210° C. to about 230° C.

EXAMPLES

Those skilled in the art will recognize that several embodiments are possible within the scope and spirit of this invention. The invention will now be described in greater detail by reference to the following non-limiting examples. The following examples further illustrate the invention but, of course, should not be construed as in any way limiting its scope.

Example 1 Preparation of an Herbal Extract Composition

A flow chart illustrating an exemplary method for preparing an herbal extract composition comprising (including consisting essentially of or consisting of) an extract of *Radix Aconiti, Radix Aconiti Kusnezoffii, Rhizoma et Radix Notopterygii* and *Radix Angelicae Pubescentis* is shown in FIG. 1, and described below.

The following steps were performed to prepare the herbal extract composition. The quality of *Radix Aconiti* roots, *Radix Aconiti Kusnezoffii* roots, *Rhizoma et Radix Notopterygii* roots and *Radix Angelicae Pubescentis* roots were inspected according to quality standards set forth by Chinese Pharmacopoeia. The roots were then sliced into approximately 1 cm-thick slices. Then, about 1 kg of *Radix Aconiti* root slices, about 1 kg of *Radix Aconiti Kusnezoffii* root slices, about 1 kg of *Rhizoma et Radix Notopterygii* root slices and about 1 kg of *Radix Angelicae Pubescentis* root slices were weighed out. The weighed *Radix Aconiti, Radix Aconiti Kusnezoffii, Rhizoma et Radix Notopterygii* and *Radix Angelicae Pubescentis* (starting material, herbal mixture) were optionally ground to a powder form and boiled for 5 minutes in water. The ground and boiled mixture was air-dried and about 2-5 times (such as about 3 times) of a plant oil by weight of the starting materials is then added, and the resulting mixture was heated at about 60° C. to about 100° C. (such as about 80° C.) for about 6 to about 10 hours (such as about 8 hours) in an industrial heater. The heating process extracted the active ingredients into the plant oil, giving rise to a liquid herbal extract. The liquid extracts were then filtered through a series of strainer, starting from a 1 mm strainer, to a 100 µm strainer, followed by a 50 µm strainer and finally a 10 µm strainer. An herbal extract composition is thus formulated in the filtered plant oil and collected in sealed containers.

Example 2 In Vivo Efficacy Determination

To determine the therapeutic efficacy of the herbal extract composition, the herbal extract composition as formulated in a vegetable oil was tested in a murine model of collagen-induced arthritis (labeled as formulation #4). Formulation #10 comprises an extract disclosed previously (Ye at al. (2016) *Exp Mol Pathol;* 100(2): 307-311; Ye et al. (2016) *Exp Mot Pathol;* 101(3): 341-345). Formula #4, and formula #10 were soaked onto patches respectively.

To induce arthritis in a mouse model, DBA/1J mice were injected subcutaneously at the base of the tail with a collagen/CFA emulsion on Day 0 and Day 21. To prepare the collagen/CFA emulsion for use on Day 0, 2 mL collagen was emulsified with 2 mL Complete Freund's adjuvant (CFA, Chondrex, Inc., 4 mg/ml *Mycobacterium tuberculosis*) on an ice bath. Stability of the emulsion was confirmed by non-dispersion of emulsion droplet when floated on water. At day 0, the mice were weighed and 55 of the mice available for the study were injected subcutaneously at the base of the tail with 50 µL of the collagen/CFA emulsion. Five mice were left as non-diseased controls. To prepare the collagen/CFA emulsion for use on Day 21, 2 mL collagen was emulsified with 2 mL Incomplete Complete Freund's adjuvant (ICFA, Sigma, Cat. F5506, lot SLBT0114) on an ice bath. Stability of the emulsion was confirmed by non-dispersion of emulsion droplet when floated on water. On Day 21, the mice were again weighed and 55 of the mice available for the study were injected subcutaneously at the base of the tail with 50 µL of the collagen/ICFA emulsion. Five mice were left as non-diseased controls.

The mice were weighed weekly (from Day 22 to Day 30) or weighed 3 times weekly (from Day 31 onwards) and scored for signs of arthritis daily. Briefly, each paw was scored and the sum of all four scores was recorded as the Arthritic Index (AI). Each paw was scored as follows: a score of 0 indicates no visible effects of arthritis; a score of 1 indicates edema and/or erythema of one digit; a score of 2 indicates edema and/or erythema of 2 joints; a score of 3 indicates edema and/or erythema of more than 2 joints; a score of 4 indicates severe arthritis of the entire paw and digits including limb deformation and ankylosis of the joint. The maximum possible AI is 16.

Starting from Day 31, the mice were scored for signs of arthritis and assigned to experimental groups listed in Table 1, based upon average AI. The mice were shaved at the nape of the neck. Briefly, in Group 2 (diseased, vegetable oil), the mice were administered with daily topical application of 100 µL of vegetable oil, applied transdermally via a patch soaked with vegetable oil and bandaged to the mouse neck. In Group 3, the mice were administered with daily topical application of 100 µL of #4 formulated in vegetable oil, applied transdermally via a patch soaked with formula #4 and bandaged to the mouse neck. In Group 4, the mice were administered with daily topical application of 100 µL of #10 formulated in vegetable oil, applied transdermally via a patch soaked with formula #10 and bandaged to the mouse neck. In group 5, the mice were administered with daily subcutaneous injection of ENBREL® (Immunex Corporation) at a dose of 3 mg/kg of mouse weight. ENBREL® is a TNF-blocking biologic treatment that is FDA approved for treating moderate to severe rheumatoid arthritis.

TABLE 1

Treatment groups in mouse model with collagen-induced arthritis
Treatment Groups

| Group | Collagen/CFA | Test Material | Dose | Route of Administration |
|---|---|---|---|---|
| 1 | No | naïve | N/A | N/A |
| 2 | Yes | Vegetable oil | 100 µl | topical |
| 3 | Yes | #4 | 100 µl | topical |
| 4 | Yes | #10 | 100 µl | topical |
| 5 | Yes | ENBREL ® | 3 mg/kg | Subcutaneous injection |

After fourteen days of therapy the mice were weighed and scored for signs of disease. Subsequently, all mice were anesthetized and exsanguinated into pre-chilled EDTA-treated microtainer tubes (Becton Dickinson) and processed to plasma which was stored in labeled Eppendorf tubes at −80° C. The limbs were individually removed to 15 mL 10% neutral buffered formalin (Richard-Allan Scientific). The remainders of the carcasses were disposed of.

Figure 2:
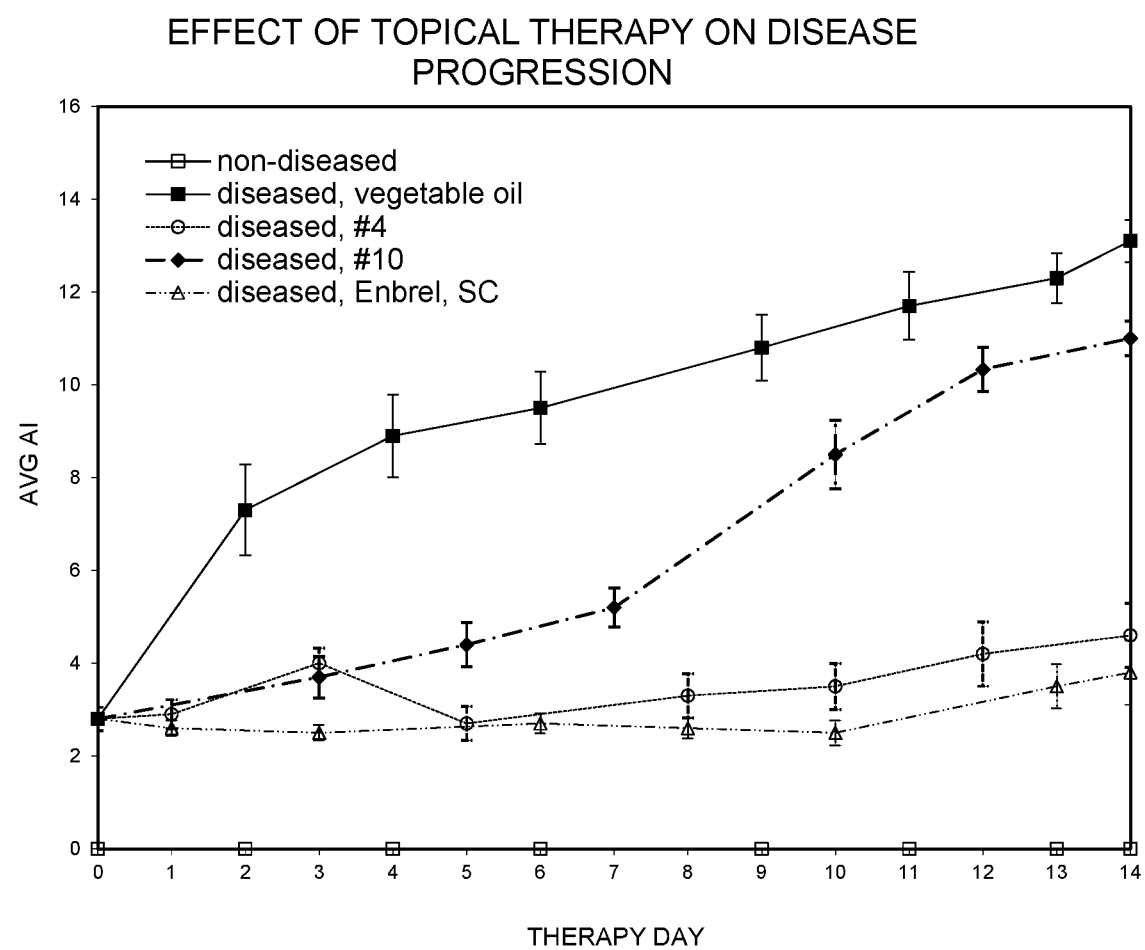
FIG. 2 shows the effect of an herbal extract composition prepared from a mixture of Radix Aconiti, Radix Aconiti Kusnezoffii, Rhizoma et Radix Notopterygii and Radix Angelicae Pubescentis (formulation #4) on the progression of arthritis in a collagen-induced DBA/1J mouse model. ENBREL®, a drug that suppresses the immune system, is used as a positive control.

The effect of the herbal extract composition on overall arthritis severity is shown in FIG. 2. In the vegetable oil-treated diseased group (Group 2), an arthritis severity score (AI) of 13.1 was observed after 14 days of treatment. No adverse effects due to daily topical administration of vegetable oil were observed. In mice treated with formulation #4 (Group 3), the rate of disease progression was reduced and after 14 days, a significant 65% reduction in arthritis severity score (AI) was recorded, as compared to mice in Group 2 (diseased, vegetable oil). In mice treated with #10 (Group 3), the rate of disease progression was reduced from Day 0 to Day 7 but was only mildly suppressed from Day 7 to Day 14, and a 16% reduction in arthritis severity score (AI) was recorded after 14 days, as compared to mice in Group 2 (diseased, vegetable oil). In mice treated with ENBREL® (positive control), disease progression was swiftly arrested. At the termination of the study, a significant 71% reduction in overall disease severity was recorded, as compared to mice in Group 2 (diseased, vegetable oil).

Figure 3:
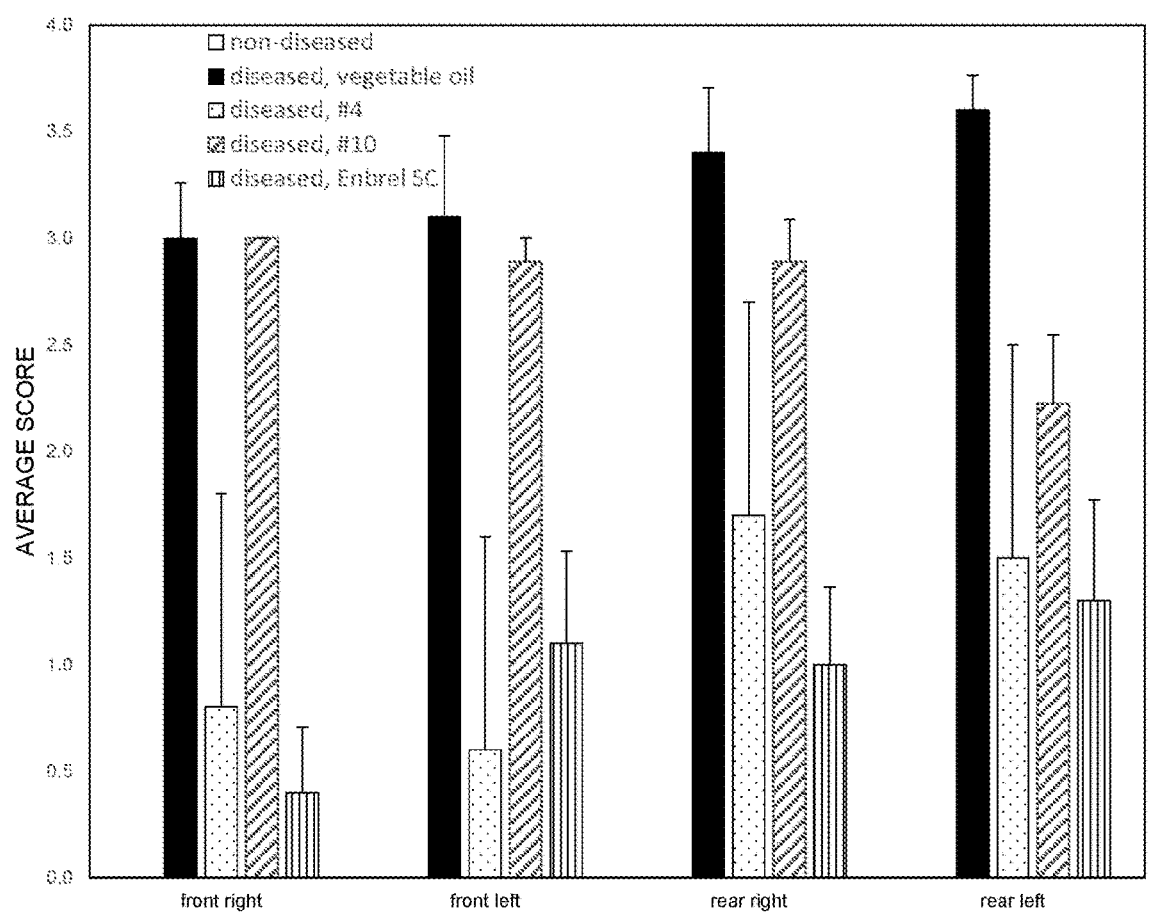
FIG. 3 shows the effect of an herbal extract composition prepared from a mixture of Radix Aconiti, Radix Aconiti Kusnezoffii, Rhizoma et Radix Notopterygii and Radix Angelicae Pubescentis (formulation #4) on the average arthritis score in each paw of a collagen-induced DBA/1J mouse model at the end of treatment cycle. ENBREL®, a drug that suppresses the immune system, is used as a positive control.

The effect of the herbal extract composition on arthritis severity in each paw at the end of 14 days was also measured, and displayed in FIG. 3 as the average AI score for each paw (front right, front left, rear right, and rear left) for each group. As shown in FIG. 3, diseased mice treated with formula #4 displayed a marked decrease in average AI score for each paw as compared to diseased mice treated with vegetable oil control. Also as shown in FIG. 3, diseased mice treated with positive control ENBREL® also displayed a similar decrease in average AI score for each paw as compared to diseased mice treated with vegetable oil control.

As shown in FIG. 2 and FIG. 3, formulation #4 (herbal extract composition prepared from a mixture comprising *Radix Aconiti, Radix Aconiti Kusnezoffii, Rhizoma et Radix Notopterygii* and *Radix Angelicae Pubescentis*) displayed similar efficacy as ENBREL® in suppressing arthritis progression in a collagen-induced arthritis mouse model.

What is claimed is:

1. An herbal extract composition comprising an extract of an herbal medicine mixture consisting of a plurality of herbal medicine, wherein the plurality of herbal medicine consists of about 20-30% (w) *Radix Aconiti*, about 20-30%

(w) *Radix Aconiti Kusnezoffii*, about 20-30% (w) *Rhizoma et Radix Notopterygii* and about 20-30% (w) *Radix Angelicae Pubescentis*.

2. The herbal extract composition of claim 1, further comprising a plant oil.

3. The herbal extract composition of claim 2, wherein the composition comprises about 50-80% of plant oil by weight.

4. A method for preparing an herbal extract composition from a mixture consisting of *Radix Aconiti, Radix Aconiti Kusnezoffii, Rhizoma et Radix Notopterygii* and *Radix Angelicae Pubescentis*, the method comprising:
   i) adding a plant oil to the mixture consisting of about 20-30% (w) *Radix Aconiti*, about 20-30% (w) *Radix Aconiti Kusnezoffii*, about 20-30% (w) *Rhizoma et Radix Notopterygii* and about 20-30% (w) *Radix Angelicae Pubescentis* to obtain a mixture in oil;
   ii) heating said mixture in oil at a temperature from about 60° C. to about 200° C., for about 5 minutes to about 10 hours;
   iii) collecting a liquid extract from the heated mixture; and
   iv) optionally mixing the liquid extract with a polymer.

5. The method of claim 4, wherein: the smoke point of the plant oil is from about 120° C. to about 300° C.; and/or the mixture in oil is heated to about 30-50% of the smoke point temperature of the plant oil; and/or the plant oil is refined, semi-refined or unrefined.

6. An herbal extract composition of claim 1, further comprising an excipient.

7. An herbal extract composition of claim 6, wherein the excipient comprises one or more polymers.

8. An herbal extract composition of claim 1, wherein the herbal extract composition is in the form of a patch.

9. A method of treating a disease of an individual, wherein the method comprises administering to the individual a therapeutically effective amount of an herbal extract composition of claim 1.

10. The method of claim 9, wherein: the disease is an autoimmune or autoinflammatory disease; and/or the disease is an acute or chronic inflammatory disease.

11. The method of claim 9, wherein: the disease is selected from the group consisting of: rheumatoid arthritis (RA), osteoarthritis (OA), active polyarticular juvenile idiopathic arthritis (JIA), and psoriatic arthritis; and/or the disease is selected from the group consisting of: sciatica, back pain, knee pain and pain caused by muscle strain.

12. The method of 11, wherein the disease is rheumatoid arthritis.

13. The method of claim 9, wherein the herbal extract composition is administered transdermally.

14. The method of claim 9, wherein the individual is human.

15. A composition comprising a plurality of herbal medicine consisting of 20-30% (w) *Radix Aconiti*, 20-30% (w) *Radix Aconiti Kusnezoffii*, 20-30% (w) *Rhizoma et Radix Notopterygii* and 20-30% (w) *Radix Angelicae Pubescentis*.

\* \* \* \* \*